United States Patent
Okumura et al.

(10) Patent No.: US 6,713,482 B2
(45) Date of Patent: Mar. 30, 2004

(54) BENZIMIDAZOLE CYCLOOXYGENASE-2 INHIBITORS

(75) Inventors: Yoshiyuki Okumura, Aichi-ken (JP); Yoshinori Murata, Aichi-ken (JP); Takashi Mano, Aichi-ken (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/924,351

(22) Filed: Aug. 8, 2001

(65) Prior Publication Data

US 2003/0013886 A1 Jan. 16, 2003

Related U.S. Application Data

(62) Division of application No. 09/244,875, filed on Feb. 5, 1999, now Pat. No. 6,310,079.

(51) Int. Cl.[7] .................. A61K 3/506; C07D 403/04
(52) U.S. Cl. .................. 514/256; 514/255; 514/247; 544/333; 544/405; 544/238
(58) Field of Search .................. 544/333, 238, 544/405; 514/256, 255, 247

(56) References Cited

U.S. PATENT DOCUMENTS

| | | | |
|---|---|---|---|
| 4,563,455 A | 1/1986 | Ueda et al. | 514/241 |
| 4,812,460 A | 3/1989 | Lazer | 514/277 |
| 6,310,079 B1 | 10/2001 | Okumura et al. | 514/338 |

FOREIGN PATENT DOCUMENTS

| | | | |
|---|---|---|---|
| EP | 0419210 | 9/1990 | C07D/235/30 |
| EP | 0846689 | 12/1997 | C07D/235/08 |
| EP | 0937722 | 2/1999 | C07D/401/04 |
| JP | 49081369 | 8/1974 | |
| JP | 59 75257 | 4/1984 | |
| JP | 3219232 | 1/1990 | |
| JP | 6194780 | 12/1992 | |
| JP | 11263788 | 2/1999 | |
| WO | WO9835977 | 2/1998 | C07H/19/04 |

OTHER PUBLICATIONS

CA 131:252564, Shinno et al. 1999.*
I. Kawasaki et al., Bulletin of the Chemical Society of Japan, vol. 44, 1971, pp. 1986–1987, Preparation of 1,7–Bis(p–hydrospehnyl)heptane).
P. Seguineau et al., Tetrahedron Letters, vol. 29, No. 4, 1988, pp. 477–480, "The Witting–Homer Reaction of Heterogeneous Media".
P.J. Sanfilippo et al., J. Med. Chem., 31, 1988, pp. 1778–1785, Synthesis of (Aryloxy)alkylamines.
Y. Amino et al., Chem. Pharm. Bull., 36(11), 1988, pp. 4426–4434 Phenylalanine Derivatives Enhancing Intestinal Absorption of.
B.E. Maryanoff et al., Chem. Rev., 1989, 89, pp. 863–927, "The Wittig Olefination Reaction and Modifications Involving Phosphoryl–Stabilized Carbanions. Stereochemistry, Mechanism, and Selected Synthetic Aspects".
J. Vallgarda et al., J. Chem. Soc., Perkin Trans. 1, 1994, pp. 461–470, Stereoselectivity and Generality of the Palladium-–Catalysed Cyclopropanation of a,β–Unsaturated Carboxylic Acids Derivatized with Oppoizer's Sultam.

* cited by examiner

*Primary Examiner*—Zinna Northington Davis
(74) *Attorney, Agent, or Firm*—Peter C. Richardson; Gregg C. Benson; Lance Y. Liu

(57) ABSTRACT

This invention provides a compound of the following formula:

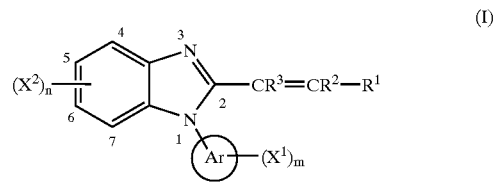

or the pharmaceutically acceptable salts thereof, wherein

Ar is heteroaryl; $X^1$ and $X^2$ are independently selected from halo, $C_1$–$C_4$ alkyl, hydroxy, $C_1$–$C_4$ alkoxy, amino, $C_1$–$C_4$ alkanoyl, carboxy, carbamoyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, or the like; $R_1$ is selected from hydrogen, straight or branched $C_1$–$C_4$ alkyl, $C_3$–$C_8$ cycloalkyl, $C_4$–$C_8$ cycloalkenyl, phenyl, heteroaryl and the like; $R^2$ and $R^3$ are independently selected from hydrogen, halo, $C_1$–$C_4$ alkyl, phenyl and the like; or $R^1$ and $R^2$ can form, together with the carbon atom to which they are attached, a $C_5$–$C_7$ cycloalkyl ring; and m and n are independently 0, 1, 2 or 3.

These compounds and pharmaceutical compositions containing such compounds are useful as analgesics and anti-inflammatory agents.

10 Claims, No Drawings

BENZIMIDAZOLE CYCLOOXYGENASE-2 INHIBITORS

This application is a division of U.S. Non-Provisional application Ser. No. 09/244,875 filed Feb. 5, 1999 now U.S. Pat. No. 6,310,079, which claims the priority benefit of PCT International Application No. IB98/00164, filed Feb. 11, 1998.

TECHNICAL FIELD

This invention relates to benzimidazole compounds and their pharmaceutically acceptable salts, and pharmaceutical compositions containing such compounds. These compounds and compositions have cyclooxygenase-2 inhibitory activities, therefore they are useful as agents for treatment of inflammatory diseases of a mammalian subject, especially a human subject.

BACKGROUND ART

Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin E2 ($PGE_2$), which is the predominant eicosanoid detected in inflammation conditions, are mediators of pain, fever and other symptoms associated with inflammation. Inhibition of biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long tern therapy can also result in severe side effects. Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. Proc. Natnl. Acad. Sci. USA, 1994, 91, 2046). COX-1 is thought to play a physiological role and to be responsible for gastrointestinal and renal protection. On the other hand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, nephrotoxicity, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme cyclooxygenase-2 and/or by intervention of the activity of the enzyme cyclooxygenase-2 on arachidonic acid would provide alternate therapy to the use of NSAIDs or corticosteriods in that such compounds would exert anti-inflammatory effects without the adverse side effects associated with COX-1 inhibition.

A variety of imidazole compounds are known and are disclosed in several patent applications. Specifically, Japanese Kokai (laid-open) Publication number S49-81369 discloses 1-benzyl-benzimidazole compounds as anti-inflammatory agents. Japanese Kokai (laid-open) Publication Number S59-75257 and H06-194780 disclose a variety of benzimidazole compounds as electrophotographic materials.

BRIEF DISCLOSURE OF THE INVENTION

The present invention provides a compound of the following formula (I):

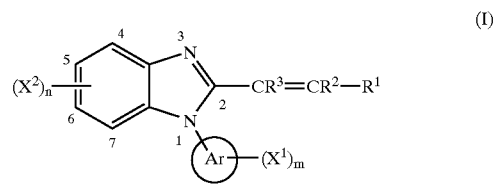

or a pharmaceutically acceptable salt thereof, wherein

Ar is heteroaryl selected from
  a 5-membered monocyclic aromatic ring having one hetero atom selected from O, S and N and optionally containing one to three N atom(s) in addition to said hetero atom, or
  a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;

$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)($C_1$–$C_4$ alkanoyl)amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)—N—($C_1$–$C_4$ alkanoyl) amino, N—[($C_1$–$C_4$ alky)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino] carbonyl, N-carbamoylamino, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino] sulfonyl and [N,N-di($C_1$–$C_4$ alkyl)amino]sulfonyl;

$R^1$ is selected from
  hydrogen;
  straight or branched $C_1$–$C_4$ alkyl optionally substituted with one to three substituent(s) wherein said substituents are independently selected from halo, hydroxy, $C_1$–$C_4$ alkoxy, amino, N—($C_1$–$C_4$ alkyl)amino and N,N-di($C_1$–$C_4$ alkyl)amino;

$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

phenyl optionally substituted with one to three substituent(s) wherein said substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—[($C_1$–$C_4$ alkyl)($C_1$–$C_4$ alkanoyl)]amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl; and heteroaryl selected from
- a 5-membered monocyclic aromatic ring having one hetero atom selected from O, S and N and optionally containing one to three N atom(s) in addition to said hetero atom; or
- a 6membered monocyclic aromatic ring having one N atom and optionally containing one to four N atom(s) in addition to said N atom; and said heteroaryl being optionally substituted with one to three substituent(s) selected from $X^1$;

$R^2$ and $R^3$ are independently selected from:
hydrogen;
halo;
$C_1$–$C_4$ alkyl,
phenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_3$–$C_7$-cycloalkyl ring;

m is 0, 1, 2, 3, 4 or 5; and n is 0, 1, 2, 3 or 4.

The benzimidazole compounds of the present invention exhibit inhibition of COX activity. Preferably, compounds of present invention exhibit inhibitory activity against COX-2, in a COX-2 selective way. Therefore, this invention also relates to a pharmaceutical composition useful as anti-inflammatory agents and analgesics, which comprises a compound of this invention and a pharmaceutically acceptable carrier.

The present invention also relates to a pharmaceutical composition for treating a disorder or condition in a mammal, selected from rheumatoid and osteoarthritis, pyrexia, asthma, bone resorption, cardiovascular diseases, nephrotoxicity, atherosclerosis, hypotension, shock, pain, cancer, Alzheimer disease, and other disorders and conditions, in which a pathological role of prostaglandins is implicated, comprising an amount of the compound of formula (1), or a pharmaceutically acceptable salt thereof, that is effective in treating such disorder or condition, and a pharmaceutically acceptable carrier.

The present invention also relates to a method of treating a disorder or condition in which prostaglandins are implicated as pathogens, in a mammalian subject, which comprises administering to a mammal an amount of compound of formula (I) or a pharmaceutically acceptable salt thereof, that is effective in treating said disorder or medical condition.

The present invention also relates to a method of treating a disorder or condition in a mammal, selected from rheumatoid and osteoarthritis, pyrexia, asthma, bone resorption, cardiovascular diseases, nephrotoxicity, atherosclerosis, hypotension, shock, pain, cancer, Alzheimer disease and other disorders and conditions, in which a pathological role of prostaglandins are implicated, comprising administering to a mammal in need of such treatment an amount of the compound of formula (I), or a pharmaceutically acceptable salt thereof, that is effective in treating such disorder or condition, and a pharmaceutically acceptable carrier.

DETAILED DISCLOSURE OF THE INVENTION

As used herein, the term "halo" means fluoro, chloro, bromo or iodo.

As used herein, the term "alkyl" means straight or branched chain saturated radicals of 1 to 4 carbon atom(s), including, but not limited to, methyl, iso-propyl, tert-butyl, and the like.

As used herein, the term "halosubstituted alkyl" refers to an alkyl radical as described above substituted with one or more halogen including, but not limited to, trifluoromethyl, and the like.

As used herein, the term "cycloalkyl" means saturated carbocyclic radicals of 3 to 8 carbon atoms, including, but not limited to, cyclopentyl, cyclohexyl, cycloheptyl and cyclooctyl.

As used herein, the term "cycloalkenyl" means carbocyclic unsaturated radicals of 4 to 8 carbon atoms, including, but not limited to, cyclopentyl, cyclohexyl, cyclohexenyl.

As used herein, a 5-membered monocyclic aromatic ring usually has one heteroatom selected from O, S and N. In addition to said heteroatom, the monocyclic aromatic ring may optionally have up to three N atoms. The 5-membered monocyclic aromatic ring includes, but not limited to thiazolyl, furyl, oxazolyl, isooxazolyl, thienyl, isothiazolyl, pyrrolyl, imidazolyl, pyrazolyl, oxadiazolyl, triazolyl, thiadiazolyl, furazanyl and tetrazolyl.

As used herein, a 6-membered monocyclic aromatic ring usually has one heteroatom which is N. In addition to said heteroatom, the monocyclic aromatic ring may optionally have up to four N atoms. The 6-membered monocyclic aromatic ring includes, but not limited to, pyridyl, pyrimidinyl, pyrazinyl, pyridazinyl and triazinyl. Preferably, $X^1$ is attached to 3, 4, 5 and 6-positions of the heteroaryl ring and $X^2$ is attached to 4, 5 and 6-positions of the imidazole ring. More preferably, $X^1$ is attached to 6-position of the heteroaryl ring and $X^2$ is attached to 5 and 6-positions of the imidazole ring.

Preferred compounds of this invention are those of the formula (1) wherein

Ar is heteroaryl selected from
a 5-membered monocyclic aromatic ring having one hetero atom selected from O, S and N and optionally containing one or two N atom(s) in addition to said hetero atom, or
a 6-membered monocyclic aromatic ring having one N atom and optionally containing one to three N atom (s) in addition to said N atom; and $X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alky, ($C_1$–$C_4$ alkoxy)$C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N—($C_1$–$C_4$ alkanoyl)amino, $C_1$–$C_4$ alkanoyl, carboxy, carbamoyl, [N—($C_1$–$C_4$ alkyl)amino]carbonyl, [N,N-di($C_1$–$C_4$ alkyl)amino]carbonyl, cyano, nitro, mercapto and ($C_1$–$C_4$ alkyl)thio;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N—($C_1$–$C_4$ alkanoyl)amino, [($C_1$–$C_4$ alkyl)sulfonyl] amino, $C_1$–$C_4$ alkanoyl, carboxy, carbamoyl, N-carbamoylamino, cyano, nitro, mercapto and ($C_1$–$C_4$ alkyl)thio;

$R^1$ is selected from
hydrogen;
straight or branched $C_1$–$C_4$ alkyl optionally substituted with one to three substituent(s) wherein said substituents are independently selected from halo, hydroxy, $C_1$–$C_4$ alkoxy and amino;
$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy and amino;
$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;
phenyl optionally substituted with one to three substituent (s) wherein the substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy)$C_1$–$C_4$ alkyl, halo-substituted $C_1$–$C_4$ alkoxy, amino, ($C_1$–$C_4$ alkanoyl)amino, $C_1$–$C_4$ alkanoyl, carboxy, carbamoyl, ($C_1$–$C_4$ alkyl)thio, ($C_1$–$C_4$ alkyl)sulfinyl, ($C_1$–$C_4$ alkyl)sulfonyl, and aminosulfonyl; or
heteroaryl selected from
a 5-membered monocyclic aromatic ring having one hetero atom selected from O, S and N and optionally containing one or two N atom(s) in addition to said hetero atom; or
a 6-membered monocyclic aromatic ring having one N atom and optionally containing one to three N atom (s) in addition to said N atom; wherein
said heteroaryl being optionally substituted with one to three substituent(s) selected from $X^1$ of this claim;

$R^2$ and $R^3$ are independently selected from:
hydrogen;
halo;
$C_1$–$C_4$ alkyl;
phenyl optionally substituted with one to three substituent(s) wherein the substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;
or $R^1$ and $R^2$ can form, together with the carbon atom to which they are attached, a $C_5$–$C_7$ cycloalkyl ring;

m is 0, 1, 2, 3 or 4 and
n is 0, 1, 2 or 3.

More preferred compounds of this invention are those of formula (I), wherein

Ar is selected from
a 5-membered monocyclic aromatic ring having one hetero atom selected from O, S and N and optionally containing one N atom in addition to said hetero atom, or
a 6-membered monocyclic aromatic ring having one N atom and optionally containing one or two N atom(s) in addition to said N atom; and $X^1$ is selected from halo, $C_1$–$C_4$ alkyl, halo-substituted $C_1$–$C_4$ alkyl, $C_1$–$C_4$ alkoxy, halo-substituted $C_1$–$C_4$ alkoxy, carbamoyl, [N—($C_1$–$C_4$ alkyl)amino]carbonyl, [N,N-di($C_1$–$C_4$ alkyl)amino]carbonyl and cyano;

$X^2$ is selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N-formylamino, N—($C_1$–$C_4$ alkanoyl) amino, [($C_1$–$C_4$ alkyl)sulfonyl]amino, N-carbamoylamino, cyano and nitro; and $R^1$ is selected from
$C_1$–$C_4$ alkyl optionally substituted with one to three substituents wherein said substituents are independently selected from halo, hydroxy and amino;
$C_5$–$C_7$ cycloalkyl optionally substituted with one to three substituents wherein said substituents are independently selected from halo, hydroxy and amino;
phenyl optionally substituted with one or two substituent(s), said substituents being independently selected from halo, hydroxy, $C_1$–$C_4$ alkyl, $C_1$–$C_4$ alkoxy, halo-substituted $C_1$–$C_4$ alkyl, halo-substituted $C_1$–$C_4$ alkoxy, ($C_1$–$C_4$ alkyl)thio, $C_1$–$C_4$ alkylsulfonyl and amino; or
heteroaryl optionally substituted with one or two $C_1$–$C_4$ alkyl group(s), wherein said heteroaryl being selected from
a 5-membered monocyclic aromatic ring having one hetero atom selected from O, S and N and optionally containing one N atom in addition to said hetero atom, or
a 6-membered monocyclic aromatic ring having one N atom and optionally containing one or two N atom(s) in addition to said N atom;

$R^2$ and $R^3$ are independently selected from
hydrogen;
halo;
$C_1$–$C_4$ alkyl; and
phenyl optionally substituted from halo, hydroxy, amino, $C_1$–$C_4$ alkyl and $C_1$–$C_4$ alkoxy;
or $R^1$ and $R^2$ can form, together with the carbon atom to which they are attached, a $C_{5-6}$ cycloalkyl ring;

m is 0, 1, 2 or 3; and
n is 0, 1, or 2.

More preferred compounds of this invention are those of formula (I), wherein

Ar is selected from pyridyl, pyrimidinyl, pyrazinyl thiazolyl, furyl, oxazolyl, isooxazolyl, thienyl, thiazolyl, isothiazolyl, pyrrolyl, imidazolyl, pyrazolyl and pyridazinyl;

$X^1$ is selected from halo, $C_1$–$C_4$ alkyl, halo-substituted $C_1$–$C_4$ alkyl, $C_1$–$C_4$ alkoxy, carbamoyl and cyano;

$X^2$ is selected from halo, $C_1$–$C_4$ alkyl, hydroxy, $C_1$–$C_4$ alkoxy, halo-substituted $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N-formylamino, N—($C_1$–$C_4$ alkanoyl)amino, [($C_1$–$C_4$ alkyl)sulfonyl]amino, N-carbamoylamino, cyano and nitro;

$R^1$ is selected from
  straight or branched $C_1$–$C_4$ alkyl;
  $C_5$–$C_7$ cycloalkyl;
  phenyl optionally substituted with one or two substituent(s), said substituents being independently selected from halo, hydroxy, $C_1$–$C_4$ alkyl, $C_1$–$C_4$ alkoxy, halo-substituted $C_1$–$C_4$ alkyl, ($C_1$–$C_4$ alkyl)thio and $C_1$–$C_4$ alkylsulfonyl; or
  heteroaryl optionally substituted with one or two $C_1$–$C_4$ alkyl group(s), said heteroaryl being selected from pyridyl, pyrimidinyl, pyrazinyl, pyridazinyl, thiazolyl, furyl, oxazolyl, isooxazolyl, thienyl, thiazolyl, isothiazolyl, pyrrolyl, imidazolyl and pyrazolyl;

$R^2$ is selected from hydrogen, $C_1$–$C_4$ alkyl and phenyl;

$R^3$ is selected from hydrogen, halo, $C_1$–$C_4$ alkyl and cyano; or $R^1$ and $R^2$ can form, together with the carbon atom to which they are attached, cyclohexyl; and m is 0, 1 or 2.

Particularly preferred compounds of this invention are those of formula (I), wherein Ar is heteroaryl selected from pyridyl, pyrimidinyl, pyrazinyl and thiazolyl;

$X^1$ is selected from fluoro, chloro, methyl, methoxy, trifluoromethyl, carbamoyl and cyano;

$X^2$ is selected from fluoro, methyl, hydroxy, methoxy, ethoxy, isopropoxy, trifluoromethyl, trifluoromethoxy, amino, N-methylamino, N,N-dimethylamino, N-methylsulfonylamino, N-formylamino, N-acetylamino, N-carbamoylamino, cyano and nitro;

$R^1$ is selected from methyl, isopropyl, cyclohexyl, phenyl, furyl, thienyl, pyridyl, imidazolyl and thiazolyl which are optionally substituted with one to three substituents selected from methyl, ethyl, isopropyl, methoxy, ethoxy, fluoro, chloro and hydroxy;

$R^2$ is selected from hydrogen, methyl and phenyl; or $R^1$ and $R^2$ can form, together with the carbon atom to which they are attached, cyclohexyl;

$R^3$ is selected from hydrogen, fluoro and cyano; and m is 0 or 1.

Among the compounds of formula (I), particularly preferred individual compounds are one of the following:

(E)-1-(2-Pyridyl)-2-styryl-1H-benzimidazole or salts thereof;

(E)-1-(4-Pyridyl)-2-styryl-1H-benzimidazole or salts thereof;

(E)-1-(2-Pyrimidyl)-2-styryl-1H-benzimidazole oxalate or salts thereof;

(E)-2-(2-Fluorostyryl)-1-(2-pyridyl)-1H-benzimidazole hydrochloride;

(E)-2-(2,6-Difluorostyryl)-1-(2-pyridyl)-1H-benzimidazole hydrochloride;

(E)-2-[2-(Cyclohexyl)ethenyl]-1-(2-pyridyl)-1H-benzimidazole or salts thereof;

(E)-2-[2-(3-Furyl)ethenyl]-1-(2-pyridyl)-1H-benzimidazole or salts thereof;

(E)-1-(2-Pyridyl)-2-[2-(2-thienyl)ethenyl]-1H-benzimidazole or salts thereof;

(E)-5-Methyl-1-(2-pyridyl)-2-styryl-1H-benzimidazole or salts thereof;

(E)-5-Fluoro-1-(2-pyridyl)-2-styryl-1H-benzimidazole or salts thereof;

(E)-1-(2-Pyridyl)-2-styryl-5-methoxy-1H-benzimidazole oxalate;

(E)-2-[2-(Cyclohexyl)ethenyl]-5-methyl-1-(2-pyridyl)-1H-benzimidazole oxalate;

(E)-2-[2-(3-Furyl)ethenyl]-5-methyl-1-(2-pyridyl)-1H-benzimidazole oxalate;

(E)-5-Methyl-1-(2-pyridyl)-2-[2-(2-thienyl)ethenyl]-1H-benzimidazole oxalate;

(E)-2-[2-(Cyclohexyl)ethenyl]-5-fluoro-1-(2-pyridyl)-1H-benzimidazole or salts thereof;

(E)-2-[2-(3-Furyl)ethenyl]-1-(2-pyridyl)-5-methoxy-1H-benzimidazole oxalate; and (E)-5-Methoxy-2-[2-(2-methyl-3-furyl)ethenyl]-1-(2-pyridyl)-1H-benzimidazole or salts thereof Most preferred individual compounds of this invention are one of the following:

(E)-2-[2-(Cyclohexyl)ethenyl]-1-(2-pyridyl)-1H-benzimidazole or salts thereof;

(E)-5-Fluoro-1-(2-pyridyl)-2-styryl-1H-benzimidazole or salts thereof;

(E)-1-(2-Pyridyl)-2-styryl-5-methoxy-1H-benzimidazole oxalate;

(E)-5-Methyl-1-(2-pyridyl)-2-[2-(2-thienyl)ethenyl]-1H-benzimidazole oxalate;

(E)-2-[2-(Cyclohexyl)ethenyl]-5-fluoro-1-(2-pyridyl)-1H-benzimidazole or salts thereof; and (E)-5-Methoxy-2-[2-(2-methyl-3-furyl)ethenyl]-1-(2-pyridyl)-1H-benzimidazole or salts thereof.

General Synthetic Method

A compound of formula I may be prepared by any synthetic procedure applicable to structure-related compounds known to those skilled in the art. The following representative examples as described in Schemes I–VI are illustrative of the invention in which, unless otherwise stated, Ar, $R^1$, $R^2$, $R^3$, $X^1$, $X^2$, m and n are as defined herein before. For the synthesis of compounds of related-structure to compounds of the present invention, see "Benzimidazoles and Congeneric Tricyclic Compounds" in *Heterocyclic Compounds*, Vol. 40, Preson, P. N. Ed., John Wiley & Sons, NY, 1981.

Scheme A

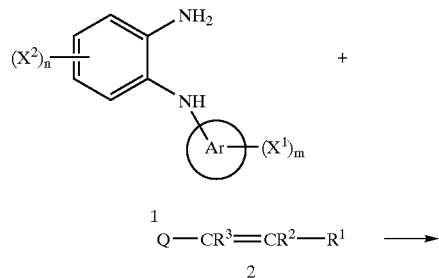

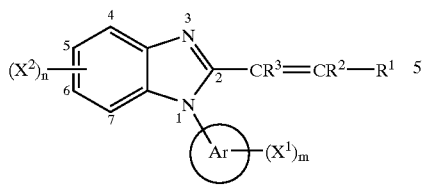

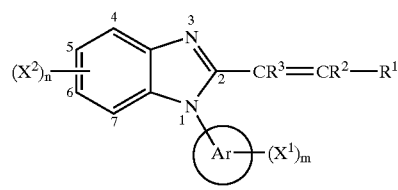

For example, the compound of formula I may be prepared according to the reaction outlined in Scheme A. In the instant example, a phenylenediamine compound of formula 1 is reacted with a compound of formula 2 wherein the group Q is defined such that the compound of formula 2 is, but not limited to, a carboxylic acid, a carboxylic acid ester, a carboxamide, a carboxylic acid anhydride, a carboxylic acid chloride, an orthoester, an imino ether or a carboxaldehyde. The reaction may be conducted in the presence or absence of a reaction inert solvent. Preferred reaction inert solvents include, but are not limited to, benzene, toluene, xylene, pyridine, 1,2-dichloroethane, o-dichlorobenzene, nitrobenzene, dichloromethane and the like. Preferably, the reaction is conducted in the presence of a promoter such as hydrochloric acid, polyphosphoric acid, phosphorous pentoxide, phosphorous oxychloride, polyphosphoric acid ethyl ether, polyphosphoric acid trimethylsilyl ether, p-toluenesulfonic acid, zinc (II) chloride and the like. When a compound of formula 2 is carboxaldehyde, the reaction may be conducted in the presence of an oxidant such as cupric acetate, chloranil, and the like. Reaction temperatures are preferably in the range of −40° C. to 250° C., more preferably 10° C. to 200° C., usually in the range of room temperature (e.g., 25° C.) to 200° C., but if necessary, lower or higher temperature can be employed. Reaction times are, in general, from 1 minute to several days, preferably from 20 minutes to 1 day. Alternatively, the reaction may be conducted in a sealed tube or an autoclave at medium to high pressure to accelerate it, preferably in the range of 2 to 150 kg/cm².

Alternatively, the compounds of formula I may be prepared by a two step procedure from phenylenediamine compounds of formula 1 via the (N-acylamino)phenylamine compounds of formula 4 as shown in Scheme B. In the first step, a phenylenediamine compound of formula 1 is reacted with a compound of formula 3, wherein Z is selected from halo, —OH, —OR (R is $C_1$–$C_4$ alkyl), —$NH_2$ or —OC(O)$CR^2$=$CR^3$—$R^1$, by conventional methods known to those skilled in the art to form amides of formula 4. For example, when a compound of formula 3 is carboxylic acid (i.e., Z is OH), the reaction is preferably conducted in the presence of a coupling reagent such as 1-(dimethylaminopropyl)-3-ethylcarbodiimide (WSC), N,N'-dicyclohexylcarbodiimide (DCC), carbonyldiimidazole, cyanophosphonic acid diethyl ester or the like. Preferred reaction-inert solvents include, but are not limited to, acetone, acetonitrile, dichloromethane, N,N-dimethylformamide, N,N-dimethylacetamide, dimethylsulfoxide, dioxane, tetrahydrofuran and pyridine. Reaction temperatures are preferably in the range of −40° C. to 250° C., more preferably 10° C. to 200° C., usually in the range of room temperature (e.g., 25° C.) to 200° C., but if necessary, lower or higher temperature can be employed.

In the next step, the compounds of formula I are provided by cyclization of the compounds of formula 4. The reaction may be conducted in the presence or absence of a reaction inert solvent. Preferred reaction inert solvents include, but are not limited to, benzene, toluene, xylene, pyridine, 1,2-dichloroethane, o-dichlorobenzene, nitrobenzene, dichloromethane and ethanol. Preferably, the reaction is conducted in the presence of a promoter such as of hydrochloric acid, polyphosphoric acid, phosphorous pentoxide, phosphorous oxychloride, polyphosphoric acid ethyl ether, polyphosphoric acid trimethylsilyl ether, thionyl chloride and p-toluenesulfonic acid. Alternatively, the cyclization reaction may be performed under Mitsunobu-type reaction conditions, for example, in the presence of triphenylphosphine and diethyl azodicarboxylate (DEAD). Reaction temperatures are preferably in the range of −40° C. to 250° C., more preferably 10° C. to 200° C., usually in the range of room temperature (e.g., 25° C.) to 200° C., but if necessary, lower or higher temperature can be employed Reaction times are, in general, from 1 minute to several days, preferably from 20 minutes to 1 day.

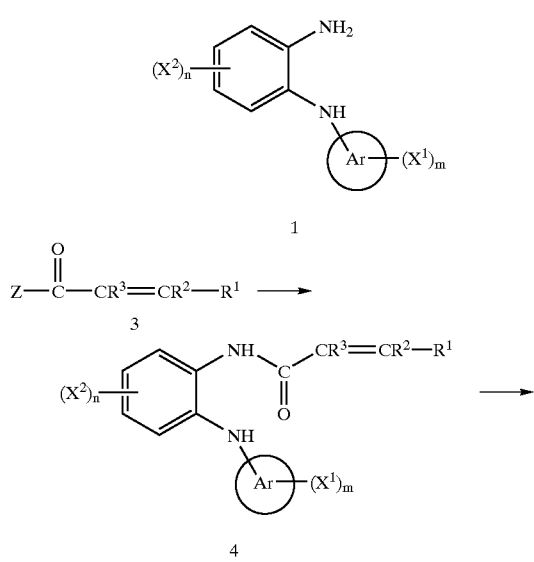

Scheme C

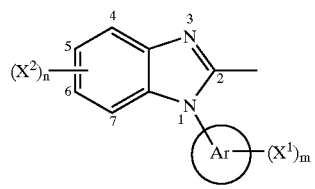 + 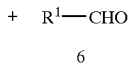 →

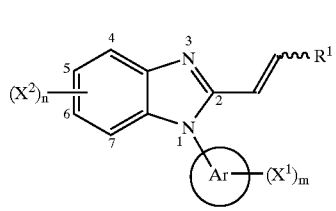

I'

Scheme D

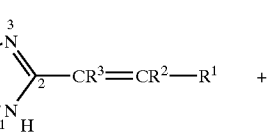 +

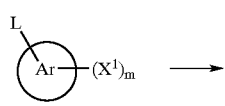 →

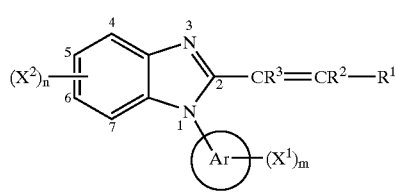

I

In another embodiment, the compounds of formula I' may be prepared as shown in Scheme C. Thus, 2-methylbenzimidazole compounds of formula 5 are reacted with aldehydes of formula 6 in the presence or absence of base (Sanfilippo, P. J.; Urbanski, M.; Press, J. B.; Hajos, Z. G.; Shriver, D. A.; Scott, C. K. *J Med Chem.,* 1988, 31, 1778). When the said reaction is conducted in the absence of base, the reaction is preferably performed in a sealed tube or an autoclave at medium to high pressure, preferably in the range of 2 to 150 kg/cm$^2$. The reaction may be conducted in the presence or absence of a reaction inert solvent. Preferred reaction inert solvents include, but are not limited to, benzene, toluene, xylene, chlorobenzene, nitrobenzene, acetic acid, acetic anhydride. Reaction temperatures are generally in the range of −100° C. to 250° C., preferably in the range of room temperature (e.g., 25° C.) to 200° C., but if necessary, lower or higher temperature can be employed. Reaction times are, in general, from 1 minute to a day, preferably from 20 minutes to 5 hours, however shorter or longer reaction times if necessary can be employed. When the said reaction is conducted in the presence of base, reaction temperatures are generally in the range of −100° C. to 250° C., preferably in the range of −80° C. to room temperature(e.g., 25° C.), but if necessary, lower or higher temperature can be employed. Preferred reaction inert solvents include, but are not limited to, THF, benzene, toluene, xylene. Reaction times are, in general, from several minutes to a day, preferably from 20 minutes to 5 hours, however shorter or longer reaction times, if necessary, can be employed. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylamine, diisopropylethylamine, piperidine or dimethylaminopyridine, or an alkyl lithium such as n-butyl lithium, sec-butyl lithium, tert-butyl lithium, methyl lithium or lithium diisopropylamide.

The compounds of formula I may also be prepared by reacting a compound of formula 7 with a compound of formula 8 according to the procedure outlined in Scheme D. In Scheme D, the compound of formula 7 may be synthesized by any of the methods described in Schemes A to C herein before. The group L of the compounds of formula 8 is a selected from a suitable displaceable group, for example, a halo or sulfonyloxy group such as fluoro, chloro, bromo, iodo, trifluoromethanesulfonyloxy, methanesulfonyloxy or p-toluenesulfonyloxy group, all readily accessible by conventional methods known to those skilled in the art. Preferably, the instant reaction is conducted in the presence of a suitable base, for example, an alkali or alkaline earth metal hydroxide, alkoxide, carbonate, or hydride, such as, but not limited to, sodium hydroxide, potassium hydroxide, sodium methoxide, sodium ethoxide, potassium tert-butoxide, sodium carbonate, potassium carbonate, sodium hydride or potassium hydride, or in the presence of an organic base an amine such as, but not limited to, triethylamine, diisopropylethylamine diisopropylamine, or dimethylaminopyridine. Preferred reaction-inert solvents include, but are not limited to, acetone, acetonitrile, dichloromethane, N,N-dimethylformamide, N,N-dimethylacetamide, dimethylsulfoxide (DMSO), dioxane, tetrahydrofuran and pyridine. Reaction temperatures are preferably in the range of −40° C. to 200° C., usually in the range of room temperature (e.g., 25° C.)to reflux temperature of solvent, but if necessary, lower or higher temperature can be employed. Reaction time is in general from 1 minute to several days, preferably from 30 minutes to 5 days. Conveniently, the reaction may be conducted in the presence of a suitable catalyst, for example, tetrakis (triphenylphosphine)-palladium(0), dichloro bis (triphenylphosphine)palladium (II), copper (0), cuprous oxide, cuprous iodide, cuprous bromide or cuprous chloride.

Scheme E

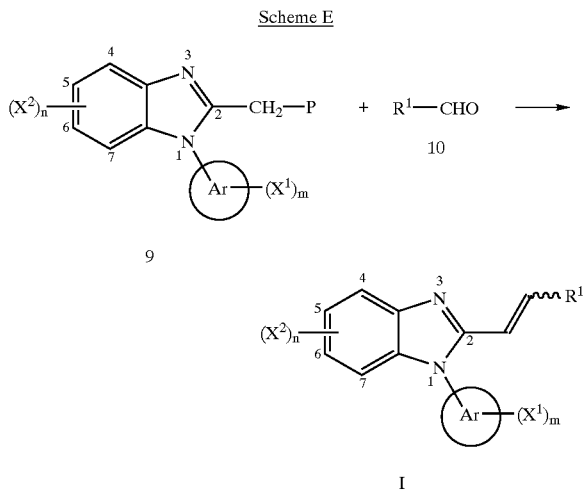

Scheme F

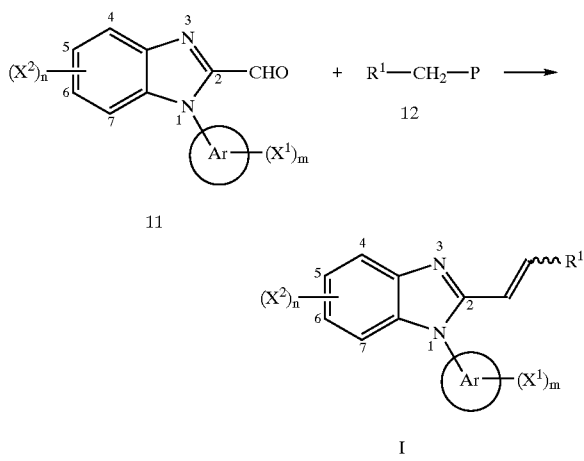

Alternatively, the compounds of formula I may be prepared by the reaction of a suitable aldehyde with a suitable phosphonium (Maryanoff, B. E.; Reitz, A. B. *Chem. Rev.* 1989, 89, 863) or a dialkyl phosphonate salt (Seguineau,; Villieras, *Tetrahedron Lett.* 1988, 29, 477) as shown in Schemes E and F, wherein P is a suitable phoshonium or dialkyl phosphonate salt. For appropriate references see DE1939809A.

The starting material of formulae 1, 2, 3, 4, 5, 6, 7, 8, 9, 10, 11 and 12 may be obtained by conventional procedures known to those skilled in the art. The preparation of such starting materials is described within the accompanying non-limiting examples which are provided for the purpose of illustration only. Alternatively, requisite starting materials may be obtained by analogous procedures, or modifications thereof described hereinafter.

The products which are addressed in the aforementioned general synthesis and illustrated in the experimental examples herein may be isolated by standard methods and purification can be achieved by conventional means known to those skilled in the art, such as distillation, recrystallization and chromatography techniques.

The compounds of the present invention which contain one or more double bonds and/or asymmetric centers are capable of existing in various steroisomeric forms. All individual forms and mixtures thereof, are included within the scope of the invention. The various isomers can be obtained by standard methods. For example, cis/trans mixtures can be separated into the individual stereoisomers by stereoselective synthesis, or by separation of the mixtures by fractional crystallization or chromatography techniques.

A majority of the compounds of the present invention are capable of forming addition salts with inorganic and organic acids. The pharmaceutically acceptable acid salts of the compounds of the present invention are those which form non-toxic addition salts, such as, but not limited to, the hydrochloride, hydrobromide, hydroiodide, nitrate, sulfate or acetate, fumalate, tartrate, succinate, maleate, glucronate, sacchariate, benzoate, methanesulfonate, benzenesulfonate, p-toluenesulfonate and pamoate (i.e., 1,1'-methylene-bis-(2-hydroxy-3-naphthoate)) salts.

The compounds of the invention which have also acidic groups are capable of forming base salts with various pharmaceutically acceptable cations. Examples of such salts include the alkali metal or alkaline earth metal salts and particularly, the sodium or potassium salts. These salts are all prepared by conventional techniques. For example, these salts can be easily prepared by treating the aforementioned compounds with an aqueous solution containing the desired pharmaceutically acceptable cation, and then evaporating the resulting solution to dryness, preferably under reduce pressure. Alternatively, they may be also be prepared by mixing together with a lower alkoxide, and then evaporating the resulting solution to dryness in the same manners as before. In either case, stoichiometric quantities of reagents are preferably employed in order to ensure completeness of reaction and maximum production of yields of the desired final product.

Biological Evaluation

The activity of the compounds of the formula (I) of the present invention, is demonstrated by the following assays.

Human umbilical vein endothelial cells (HUVEC), which is characterized by positive staining with von Willibrand's factor and an uptake of acetylated low-density lipoproteins, is available from Morinaga Bioscience Lab., Yokohama, Japan. HUVEC is maintained in E-GM UV (from Kurashikibouseki Co., Neyagawa, Japan) in 5% $CO_2$/95% air at 37° C. $PGE_2$, thromboxane $B_2$ ($TXB_2$) and 6-keto prostaglandin $F_{1\alpha}$ (6-keto-$PGF_{1\alpha}$) are available from Cayman Chemical Co. (Ann Arbor, USA). Recombinant human interleukin-1β (hIL-1β) is available from R&D Systems (Minneapolis, USA). RIA kits for $PGE_2$, $TXB_2$ and 6-keto-$PGF_{1\alpha}$ is available from Amersham (Tokyo, Japan). Indomethacin and other reagents used herein are available from Sigma Chemical Co. (St. Louis, USA) unless specified otherwise. Dexamethasone (sold under the trade name of decadron) is available from Banyu Pharmaceutical Co. (Tokyo, Japan). A blood collection tube sold under the trade name of Vacutainer is available from Becton Dickinson (Bedford, USA). Male Sprague-Dawley rats are available from Charles River (Hino, Japan).

In Vitro Assays

Human Cell-based COX-1 Assay

Human cell based COX-1 assay is carried out essentially according to a previously described procedure (Grossman et al., *Inflam. Res.*, 1995, 44, 253). Human peripheral blood obtained from healthy volunteers using Vacutainer is diluted to 1/10 volume with 3.8% sodium citrate solution. The platelet-rich plasma immediately obtained is washed with 0.14 M sodium chloride containing 12 mM Tris-HCl (pH 7.4) and 1.2 mM EDTA. Platelets are then washed with platelet buffer (Hanks buffer (Ca free) containing 0.2% BSA and 20 mM Hepes). Finally, the human washed platelets (HWP) are suspended in platelet buffer at the concentration of $2.85 \times 10^7$ cells/ml and stored at room temperature until use. The HWP suspension (70 µl aliquots, final $2.0 \times 10^7$ cells/ml) is placed in a 96-well U bottom plate and 10 µl aliquots of 12.6 mM $CaCl_2$ added. Platelets are incubated with A23187 (final concentration; 10 µM, Sigma) with test compound (0.1–100 µM) dissolved in DMSO (final concentration; less than 0.01%) at 37° C. for 15 min. The reaction is stopped by addition of EDTA (final concentration; 7.7 mM) and $TXB_2$ in the supernatant quantitated by using a radioimmunoassay kit (Amersham) according to the manufacturer's procedure.

Human cell-based COX-2 Assay

Inhibition of COX-2 Activity After Induction of COX-2 by hIL-1β

The human cell based COX-2 assay is carried out as previously described (Moore et al., *Inflam. Res.*, 1996, 45, 54). Confluent human umbilical vein endothelial cells (HUVECs, Morinaga) in a 96-well U bottom plate are washed with 100 µl of RPMI1640 containing 2% FCS and incubated with hIL-1β (final concentration; 300 U/ml, R & D Systems) at 37° C. for 24 hr. After washing, the activated HUVECs are stimulated with A23187 (final concentration; 30 µM) in Hanks buffer containing 0.2% BSA, 20 mM Hepes and test compound (0.1 nM–100 µM) dissolved in DMSO (final concentration; less than 0.01%) at 37° C. for 15 min. 6-keto-$PGF_{1\alpha}$, stable metabolite of $PGI_2$ (prostaglandin $I_2$), in the supernatant is quantitated after adequate dilution by using a radioimmunoassay kit (Amersham) according to the manufacturer's procedure.

Inhibition of COX-2 During the Induction Phase

Confluent human umbilical vein endothelial cells (HUVECs, Morinaga) in a 96-well U bottom plate are washed with 100 µl of RPMI1640 containing 2% FCS and test compound (0.1 nM–100 µM) dissolved in DMSO (final concentration; less than 0.01%), and incubated with hIL-1β (final concentration; 300 U/ml, R & D Systems) at 37° C. for 24 hr. After washing, the HUVECs are stimulated with A23187 (final concentration 30 µM) in Hanks buffer containing 0.2% BSA and 20 mM Hepes at 37° C. for 15 min. 6-keto-$PGF_{1\alpha}$, a stable metabolite of prostaglandin $I_2$ ($PGI_2$), in the supernatant is quantitated after adequate dilution by using a radioimmunoassay kit (Amersham) according to the manufacturer's procedure.

In Vivo Assays

Carrageenan Induced Foot Edema in Rats

Male Sprague-Dawley rats (5 weeks old, Charles River Japan) are fasted overnight. A line is drawn using a marker above the ankle on the right hind paw and the paw volume (V0) is measured by water displacement using a plethysmometer (Muromachi). Animals are given orally either vehicle (0.1% methyl cellulose or 5% Tween 80) or a test compound (2.5 ml per 100 g body weight). One hour later, the animals are then injected intradermally with λ-carrageenan (0.1 ml of 1% w/v suspension in saline, Zushikagaku) into right hind paw (Winter et al., *Proc. Soc. Exp. Biol. Med,* 1962, 111, 544; Lombardino et al., *Arzneim. Forsch.,* 1975, 25, 1629) and three hours later, the paw volume (V3) is measured and the increase in volume (V3–V0) calculated. Since maximum inhibition attainable with classical NSAIDs is 60–70%, $ED_{30}$ values are calculated.

Measurement of $PGE_2$ in Inflammatory Site and Stomach in Rats

Determination of $PGE_2$ synthesized in the inflammatory site is carried essentially according to a previously described method (Opas et al., *Biochem. Pharmacol,* 1987, 36, 547). Foot edema in male Sprague-Dawley rats (5 weeks old) is induced by subplanter injection of 0.1 ml of 1% w/v λ-carrageenan suspension. Animals are sacrificed by cervical dislocation 3 h following carrageenan injection. The foot is amputated, frozen in liquid nitrogen and stored at −80° C. until analysis. The stomach of these animals are excised, frozen in liquid nitrogen and stored at −80° C. until analysis. The frozen foot is crushed, mixed with 7 ml of ethanol containing 10 µg/ml of indomethacin, pulverized in a Waring blender and clarified by centrifugation at 3,000 r.p.m. for 10 min. at 4° C. The frozen stomach is mixed with 7 ml of ethanol containing 10 µg/ml of indomethacin, homogenized by Polytrone and clarified by centrifugation at 3,000 r.p.m. for 10 min. at 4° C. $PGE_2$ is extracted by a solid-phase extraction devices sold under the trade name of Sep-Pak $C_{18}$ cartridge (from Waters, Milford, USA) and dried in vacuum. Samples are diluted to a final volume of 0.5 ml with assay buffer (PBS containing 0.1% w/v gelatin) and the level of $PGE_2$ is quantitated after adequate dilution by using a radioimmunoassay kit (Amersham) according to the manufacturer's procedure. Test compounds are suspended in 0.1% w/v methylcellulose and dosed 1 h before carrageenan injection. Dexamethasone is dissolved in saline and administered subcutaneously 3 h before carrageenan injection.

Gastric Ulceration in Rats

The gastric ulcerogenicity of test compound is assessed by a modification of the conventional method (Ezer el al., *J. Pharm. Pharmacol,* 1976, 28, 655; Cashin et al., *J. Pharm. Pharmacol.,* 1977, 29, 330). Male Sprague-Dawley rats (5 weeks old, Charles River Japan), fasted overnight, are given orally either vehicle (0.1% methyl cellulose or 5% Tween 80) or a test compound (1 ml per 100 g body weight). Six hours after, the animals are sacrificed by cervical dislocation. The stomachs are removed and inflated with 1% formalin solution (10 ml). Stomachs are opened by cutting along the greater curvature. From the number of rats that show at least one gastric ulcer or haemorrhaging erosion (including ecchymosis), the incidence of ulceration is calculated. Animals do not have access to either food or water during the experiment. The half-ulcerogenic dose ($UD_{50}$) value, i.e., dose required to induce at least one gastric lesion or one hemorrhagic erosion in 50% of the animals tested, is calculated by non-linear equation; % Control=100/(1+ [Dose]/$UD_{50}$).

Data Analysis

Statistical program packages, SYSTAT (SYSTAT, INC.) and StatView (Abacus Cencepts, Inc.) for Macintosh were used. Differences between test compound treated group and control group are tested for using ANOVA. The $IC_{50}$, $ED_{30}$ or $UD_{50}$ values are calculated from the equation for the log-linear regression line of concentration (dose) versus percent inhibition.

In these testings, some compounds indicated low $IC_{50}$ values, in the range of 0.01 to 1.0 µM.

The compounds of the formula (I) of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of above-mentioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The following examples contain detailed descriptions of the methods of the preparation of compounds of formula I. These detailed descriptions fall within the scope, and serve to exemplify, the above described General Synthetic Procedures which form part of the invention. These detailed descriptions are presented for illustrative purposes only and are not intended as a restriction in thee scope of the invention.

EXAMPLES AND PREPARATIONS

The present invention is illustrated by the following examples and preparations. However, it should be understood that the invention is not limited to the specific details of these examples and preparations. Unless otherwise stated, all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (TLC) and reaction times are given for illustration only; melting points (m.p.) given are uncorrected (polymorphism may result in different melting points); structure and purity of all isolated compounds were assured by at least one of the following techniques: TLC (Merck silica gel 60 F-254 precoated plates), mass spectrometry, nuclear magnetic resonance (NMR) or microanalysis. Yields are given for illustrative purposes only. Flash column chromatography was carried out using Merck silica gel 60 (230–400 mesh ASTM). NMR data was determined at 270 MHz (JEOL GX 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc.

Example 1

(E)-1-(2-Pyridyl)-2-styryl-1H-benzimidazole

Method A

To a stirred solution of N-(2-pyridyl)-o-phenylenediamine (0.46 g, 2.4 mmol; Stephenson, L.; Warburton, W. K. *J. Chem. Soc. C,* 1970, 1355) in toluene (50 ml) was added (E)-cinnamoyl chloride (0.40 g, 2.4 mmol) and the resulting mixture was heated to reflux removing water using a Dean-Stark apparatus for 13 h. After cooling, the reaction mixture was concentrated to dryness. The residue was dissolved into ethyl acetate (100 ml), washed consecutively with saturated aqueous sodium bicarbonate solution (50 ml) and brine (50 ml), dried (magnesium sulfate) and concentrated to dryness. Column chromatography (silica gel, 95 g; n-hexane/ethyl acetate (2/1)) followed by recrystallization from isopropyl ether yielded 0.29 g (41%) of the titled compound.

Method B

To a stirred suspension of sodium hydride (0.48 g, 12 mmol) in dimethylacetamide (20 ml) at 0° C. under a nitrogen atmosphere was added a solution of (E)-2-styryl-1H-benzimidazole (2.20 g, 10 mmol; Roseman, S. *J. Am. Chem. Soc.,* 1953, 75, 3854) in dimethylacetamide (30 ml) during 10 min. The reaction mixture was allowed to warm to room temperature and then a solution of 2-fluoropyridine (1.46 g, 15 mmol) in dimethylacetamide (10 ml) was added. The resulting mixture was heated at reflux for 5 h, cooled and quenched by adding saturated ammonium chloride solution (1.5 ml). Volatiles were removed by evaporation under reduced pressure and the residue was partitioned between a mixture of ethyl acetate (100 ml) and water (100 ml). The separated aqueous layer was extracted with ethyl acetate (100 ml). The combined organic layers were washed consecutively with water (100 ml) and brine (100 ml), dried (magnesium sulfate) and concentrated to dryness. Column chromatography (silica gel, 300 g; n-hexane/ethyl acetate (2/1)) gave 1.91 g of solids. Recrystallization from isopropyl ether yielded 1.71 g (58%) of the titled compound as pale yellow solids. MW: 297.36; mp: 129.0–129.5° C.; $^1$H-NMR (CDCl$_3$) δ: 8.80–8.76 (1H, m), 8.05–7.96 (2H, m), 7.87–7.81 (1H, m), 7.55–7.43 (5H, m), 7.39–7.23 (5H, m), 7.15 (1H, d, J=16.1 Hz).

Example 2

(E)-1-(3-Pyridyl)-2-styryl-1H-benzimidazole

To a stirred suspension of N-(3-pyridyl)-o-phenylenediamine (0.93 g, 5 mmol; Kirsch, P.; Schoenleben-Janas, A.; Schirmer, R. H. *Liebigs Ann. Org. Bioorg. Chem.*, 1995, 7, 1275) in xylene (60 ml) was added (E)-cinnamoyl chloride (0.83 g, 5 mmol). After stirring at the room temperature for 1h, the resulting mixture was heated to reflux removing water using a Dean-Stark apparatus for 11 h. After cooling, the reaction mixture was concentrated to dryness. The residue was dissolved into ethyl acetate (100 ml), washed consecutively with saturated aqueous sodium bicarbonate solution (50 ml) and brine (50 ml), dried (magnesium sulfate) and concentrated to dryness. The residue was purified by column chromatography (silica gel, 165 g; n-hexane/ethyl acetate (3/2 to 1/1)) to give 0.77 g (34%) of brown solids. Recrystallization from isopropyl ether yielded 0.50 g of the titled compound as pink solids. MW: 297.36; mp: 118.0–118.5° C.; $^1$H-NMR (CDCl$_3$) δ: 8.84 (1H, dd, J=4.8, 1.5 Hz), 8.79 (1H, d, J=2.6 Hz), 8.00 (1H, d, J=15.8 Hz), 7.88–7.79 (2H, m), 7.61 (1H dd, J=8.1, 4.8 Hz), 7.50–7.44 (2H, m), 7.39–7.15 (6H, m), 6.78 (1H, d, J=15.8 Hz).

Example 3

(E)-1-(4-Pyridyl)-2-styryl-1H-benzimidazole

A solution of N-(4-pyridyl)-o-phenylenediamine dihydrochloride (2.6 g, 10 mmol) in ethyl acetate (100 ml) was washed consecutively with a 0.5 N aqueous solution of sodium hydroxide (100 ml), water (100 ml) and brine (100 ml), dried (sodium sulfate) and concentrated in vacuo to give the free base as yellow solids. To a stirred solution of N-(4-pyridyl)-o-phenylenediamine obtained above in pyridine (50 ml) was added (E)-cinnamoyl chloride (1.7 g, 10 mmol) and the mixture was heated under reflux for 3 h. Then the volatiles were removed under reduced pressure and the residue was dissolved in chloroform (100 ml). The organic phase was washed consecutively with saturated aqueous sodium bicarbonate solution (50 ml) and brine (50 ml), dried (sodium sulfate) and concentrated in vacuo. The residue was purified by column chromatography (silica gel, 100 g; n-hexane/ethyl acetate (1/1)) and then recrystallized from ethyl acetate to afford 131 mg (4%) of the titled compound as white solids. MW: 297.36; mp: 167.8–168.8° C; $^1$H-NMR (CDCl$_3$) δ: 8.92 (2H, dd, J=4.4, 1.5 Hz), 8.01 (1H, d, J=16.1 Hz), 7.85 (1H, ddd, J=8.1, 1.8, 0.7 Hz), 7.54–7.24 (10H, m) 6.87 (1H, d, J=16.1 Hz).

Example 4

(E)-1-(3-Methylpyrid-2-yl)-2-styryl-1H-benzimidazole hydrochloride

Free base of the titled compound was prepared from 2-styryl-1H-benzimidazole and 2–Chloro-3-methylpyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate/n-hexane to give the titled compound. MW: 347.85; mp: 226.0–228.0° C.; $^1$H-NMR (DMSO-d$_6$) δ: 8.66–8.62 (1H, m), 8.21–8.14 (2H, m), 7.91 (1H, d, J=8.1 Hz), 7.76 (1H, dd, J=7.7, 4.8 Hz), 7.68–7.60 (2H, m), 7.60–7.54 (1H, m), 7.50–7.43 (4H, m), 7.26 (1H, d, J=8.1 Hz), 6.89 (1H, d, J=16.5 Hz), 2.12 (3H,s).

Example 5

(E)-2-Styryl-1-(3-trifluoromethylpyridin-2-yl)-1H-benzimidazole

To a stirred solution of (E)-2-styryl-1H-benzimidazole (0.49 g, 2.2 mmol) in dimethylacetamide (20 ml) at 0° C. under a nitrogen atmosphere was added sodium hydride (0.11 g, 2.8 mmol). After stirring at 0° C. for 20 min. and then at room temperature for 30 min., a solution of 2–Chloro-3-trifluoromethylpyridine (0.60 g, 3.3 mmol) in dimethylacetamide (5 ml) was added. The resulting mixture was heated to reflux for about 3 h 20 min. After cooling, copper bronze (0.45 g, 7.1 mg-atom) was added and heating was continued for 9 h 20 min. The reaction mixture was filtered through a pad of celite and the filtrate was diluted with dichloromethane (200 ml), washed consecutively with water (3×200 ml) and brine (100 ml), dried (magnesium sulfate) and concentrated to dryness. Purification by column chromatography (silica gel, 150 g; n-hexane/ethyl acetate (2/1)) followed by recrystallization from a mixture of isopropyl ether and n-hexane yielded 37 mg (5%) of the titled compound as white solids. MW: 365.36; mp: 156.0–157.0° C.; $^1$H-NMR (CDCl$_3$) δ: 8.96 (1H, dd, J=4.8, 1.8 Hz), 8.36 (1H, dd, J=8.1, 1.8 Hz), 7.90 (1H, d, J=15.8 Hz), 7.84 (1H, d, J=8.1 Hz), 7.76 (1H, d, J=8.1, 4.8 Hz), 7.45–7.20 (7H, m), 6.92 (1H, d, J=7.7 Hz), 6.47 (1H, d, J=15.8 Hz).

Example 6

(E)-1-(3–Cyanopyridin-2-yl-2-styryl-1H-benzimidazole hydrochloride

Free base of the titled compound was prepared from 2-styryl-1H-benzimidazole and 2–Chloro-3–Cyanopyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate to give the titled compound. MW: 334.38; mp: 171.5–172.5° C.; $^1$H-NMR (CDCl$_3$) δ: 8.98 (1H, dd, J=4.8, 1.8 Hz) 8.32 (1H, dd, J=7.7, 1.8 Hz), 7.98 (1H, d, J=16.1 Hz), 7.89–7.85 (1H, m), 7.67 (1H, dd, J=7.7, 4.8 Hz), 7.52–7.47 (2H, m), 7.42–7.26 (5H, m), 7.23–7.19 (1H, m), 6.83 (1H, d, J=16.1 Hz).

Example 7

(E)-1-(3-carbamoylpyridin-2-yl)-2-styryl-1H-benzimidazole oxalate

A stirred mixture of (E)-1-(3–Cyanopyridin-2-yl)-2-styryl-1H-benzimidazole (0.40 g, 1.2 mmol), potassium tert-butoxide (0.56 g, 5.0 mmol), water (0.09 ml, 5.0 ml), and tert-butyl alcohol (20 ml) was heated to reflux for 45 min. After cooling, the mixture was diluted with ethyl acetate (100 ml), washed consecutively with water (50 ml), and brine (50 ml), dried (magnesium sulfate) and concentrated to dryness. Column chromatography (silica gel, 150 g; ethyl acetate) gave 0.50 g of a foam. The free base and oxalic acid (135 mg, 1.5 mmol) were dissolved into a mixture of ethyl acetate (25 ml) and ethanol (10 ml). After cooling to 0° C., solids were collected by suction, washed with ethyl acetate (2×2 ml) and dried under vacuum at 50° C. overnight to give 0.33 g (64%) of the titled compound as a white powder. MW: 340.42; mp: 178.0–180.0° C. (decomposition); $^1$H-NMR (DMSO) δ: 8.81 (1H, dd, J=4.8, 1.8 Hz), 8.28 (1H, dd, J=7.7, 1.8 Hz), 8.11 (1H, br.s), 7.82(1H, d, J=16.1 Hz), 7.77 (1H, d, J=7.7, 4.8 Hz), 7.69 (1H, d, J=8.1 Hz), 7.61–7.56 (2H, m), 7.51 (1H, br.s), 7.43–7.14 (6H, m), 6.86 (1H, d, J=16.1 Hz).

Example 8

(E)-1-(4-Methylpyrid-2-yl)-2-styryl-1H-benzimidazole hydrochloride

Free base of the titled compound was prepared from 2-styryl-1H-benzimidazole and 2-fluoro-4-methylpyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate/n-hexane to give the titled compound. MW: 358.68; mp: 221.0–222.5° C.; $^1$H-NMR (DMSO) δ: 8.66 (1H, d, J=5.1 Hz), 8.22–8.15 (1H, m), 7.86 (1H, d, J=7.7 Hz), 7.71–7.66 (3H, m), 7.59–7.44 (7H, m), 7.20 (1H, d, J=16.1 Hz), 2.53 (3H, s).

Example 9

(E)-1-(5-Methylpyrid-2-yl)-2-styryl-1H-benzimidazole hydrochloride

Free base of the titled compound was prepared from 2-styryl-1H-benzimidazole and 2–Chloro-5-methylpyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate-hexane to give the titled compound. MW: 347.85; mp: 245.0–247.0° C.; $^1$H-NMR (DMSO-$d_6$) δ: 8.66 (1H, d, J=1.8 Hz), 8.19 (1H, d, J=16.1 Hz), 8.08 (1H, dd, J=8.1, 2.1 Hz), 7.87 (1H, d, J=8.8 Hz), 7.76 (1H, d, J=8.1 Hz), 7.71–7.66 (2H, m), 7.57–7.52 (2H, m), 7.49–7.44 (4H, m), 7.19 (1H, d, J=16.1 Hz), 2.50 (3H, s).

Example 10

(E)-2-Styryl-1-(5-trifluoromethylpyridin-2-yl)-1H-benzimidazole hydrochloride

A stirred mixture of 2-styryl-1H-benzimidazole (330 mg, 1.5 mmol), 2–Chloro-5-trifluoromethylpyridine (680 mg, 3.0 mmol), potassium carbonate (210 mg, 1.5 mmol), copper bronze (30 mg) and nitrobenzene (15 ml) was heated to reflux under a nitrogen atmosphere for 2.5 h. The cooled reaction mixture was directly chromatographed (silica gel, 120 g; n-hexane/ethyl acetate (4/1)) to give 510 mg of yellow oil. The product was dissolved into methanol (10 ml) and treated with a 10% methanol solution of hydrogen chloride (10 ml). Volatiles were removed under reduced pressure and the residue was recrystallized from isopropyl ether-hexane to afford 202 mg of the titled compound as light yellow needles. MW: 401.82; mp: 215.0–218.0° C.; $^1$H-NMR (DMSO) δ: 9.26–9.21 (1H, m), 8.67–8.61 (1H, m), 8.16–8.02 (2H, m), 7.87–7.81 (1H, m), 7.75–7.62 (3H, m), 7.52–7.37 (5H, m), 7.34 (1H, d, J=16.1 Hz).

Example 11

(E)-1-(6-Methylpyrid-2-yl)-2-styryl-1H-benzimidazole hydrochloride

Free base of the titled compound was prepared from 2-styryl-1H-benzimidazole and 2–Chloro-6-methylpyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate/n-hexane to give the titled compound. MW: 347.85; mp: 216.0–217.0° C.; $^1$H-NMR (DMSO-$d_6$) δ: 8.20 (1H, br s), 8.10 (1 H, t, J=7.7 Hz), 7.87 (1H, d, J=7.7 Hz), 7.71–7.44 (10H, m), 7.22 (1H, d, J=16.1 Hz), 2.63 (3H, s).

Example 12

(E)-1-(6-Fluoropyridin-2-yl)-2-styryl-1H-benzimidazole hydrochloride

Free base of the titled compound was prepared from 2-styryl-1H-benzimidazole and 2,6-difluoropyridine according to the preparation of (E)-1-(2-pyridyl)-2-styryl-1H-benzimidazole (Example 1, method B). The free base was dissolved into diethyl ether and hydrogen chloride gas was passed through the ether solution. Filtration and drying under vacuum yielded the titled compound as pale yellow solids. MW: 351.81; mp: 198.0–205.0° C.; $^1$H-NMR (DMSO-$d_6$) δ: 8.43 (1H, ddd, J=8.1, 8.1, 8.1 Hz), 8.26 (1H, d, J=16.1 Hz), 7.90–7.80 (2H, m), 7.76–7.69 (2H, m), 7.66–755 (3H, m), 7.54–7.43 (4H, m), 7.28 (1H, d, J=16.1 Hz).

Example 13

(E)-1-(6-Chloropyridin-2-yl)-2-styryl-1H-benzimidazole

Free base of the titled compound was prepared from 2-styryl-1H-benzimidazole and 2,6-dichloropyridine according to the preparation of (E)-1-(2-pyridyl)-2-styryl-1H-benzimidazole (Example 1, method B). MW: 331.81; mp: 122.0–123.0° C.; $^1$H-NMR (DMSO) δ: 8.22 (1H, t, J=7.9 Hz), 7.91 (1H, d, J=16.1 Hz), 7.79–7.72 (3H, m), 7.67–7.63 (2H, m), 7.50–7.47 (1H, m), 746–7.28 (5H, m), 7.23 (1H, d, J=16.1 Hz).

Example 14

(E)-1-(6-Methoxypyridin-2-yl)-2-styryl-1H-benzimidazole hydrochloride

According to the literature procedure (Trecourt, F.; Mallet, M.; Mongin, O,.; Queguiner, G. *J. Org. Chem.* 1994, 59, 6173.), a solution of (E)-1-(6–Chloropyridin-2-yl)-2-styryl-1H-benzimidazole (145 mg, 0.44 mmol), 28% NaOEt in MeOH (3 ml) and toluene (5 ml) was maintained at room temperature for 2 h then heated under reflux condition for 1 h. To this solution, water (1 ml) was added and it was concentrated by evaporator. To this residue , water (5 ml) was added and the whole was extracted with $CH_2Cl_2$ (2×15 ml). Combined organic layer was dried (magnesium sulfate) and filtered. The filtrate was concentrated and the residue was purified by column chromatography (silica gel, 20 g; n-hexane/ethyl acetate (5/1)) to afford the desired compound (35 mg, 24%). The free base was treated with a 10% methanol solution of hydrogen chloride and concentrated to dryness. The residue was recrystallized from ethyl acetate/n-hexane to give the titled compound. MW: 363.85; mp: 199.0–200.0° C.; $^1$H-NMR (DMSO) δ: 8.15–8.08 (2H, m), 7.85 (1H, d, J=8.1 Hz), 7.74–7.66 (3H, m), 7.56–7.20 (6H, m), 7.15 (1H, d, J=8.4 Hz), 702–7.00 (1H, m), 3.90 (3H, s).

Example 15

(E)-1-(2-Pyrimidyl)-2-styryl-1H-benzimidazole oxalate

Free base of the titled compound was prepared from 2-styryl-1H-benzimidazole and 2–Chloropyrimidine according to the preparation of (E)-1-(2-pyridyl)-2-styryl-1H-benzimidazole (Example 1, method B). The free base and oxalic acid were dissolved into ethyl acetate. Concentration and recrystallization from ethyl acetate-hexane yielded the titled compound. MW: 388.39; mp: 167.0–168.0° C.; $^1$H-NMR (DMSO-d$_6$) δ: 9.09 (2H, dd, J=5.1, 0.7), 8.13–8.07 (1H, m), 7.91 (2H, s), 7.76–7.70 (2H, m), 7.76 (1H, d, J=7.3 Hz), 7.63 (1H, td, J=4.8, 0.7 Hz), 7.41 (1H, d, J=7.7 Hz), 7.46–7.30 (4H, m).

Example 16

(E)-2-Styryl-1-(4-trifloromethyl-2-Pyrimidyl)-1H-benzimidazole oxalate

Free base of the titled compound was prepared from 2-styryl-1H-benzimidazole and 2–Chloro-4-trifluromethyl-pyrimidine according to the preparation of (E)-1-(2-pyridyl)-2-styryl-1H-benzimidazole (Example 1, method B). The free base and oxalic acid were dissolved into ethyl acetate. Concentration and recrystallization from ethyl acetate/n-hexane yielded the titled compound. MW: 411.37; mp: 189.0–191.0° C.; $^1$H-NMR (DMSO) δ: 9.42 (1H, d, J=4.8 Hz), 8.20–8.13 (1H, m), 8.10 (1H, dd, J=4.8, 1.3 Hz), 8.01 (1H, d, J=16.1 Hz), 7.91 (1H, d, J=16.1 Hz), 7.79–7.71 (1H, m), 7.68 (1H, d, J=7.0 Hz), 7.47–7.34 (6H, m).

Example 17

(E)-1-(4-Pyrimidyl)-2-styryl-1H-benzimidazole hydrochloride

Free base of the titled compound was prepared from 2-styryl-1H-benzimidazole and 4–Chloropyrimidine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate/n-hexane to give the titled compound. MW: 234.81; mp: 191.0–192.0° C.; $^1$H-NMR (CDCl$_3$) δ: 9.42 (1H, br.s), 9.15 (1H, br.s), 8.26 (1H, d, J=16.5 Hz), 8.08–7.94 (1H, m), 7.82–7.71 (4H, m), 7.58–7.33 (6H, m).

Example 18

(E)-1-(6–Chloro4-pyrimidyl)-2-styryl-1H-benzimidazole hydrochloride

Free base of the titled compound was prepared from 2-styryl-1H-benzimidazole and 4,6-dichloropyrimidine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate-hexane to give the titled compound. MW: 376.33; mp: 203.0–204.0° C.; $^1$H-NMR (DMSO) δ: 9.27 (1H, d, J=1.1 Hz), 8.15 (1H, d, J=1.1 Hz), 8.02–7.94 (1H, m), 7.80–7.72 (4H, m), 7.49–7.27 (6H, m).

Example 19

(E)-1-(2-Pyradyl)-2-styryl-1H-benzimidazole

Free base of the titled compound was prepared from 2-styryl-1H-benzimidazole and 2-chloropyradine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from ethyl acetate-hexane to give the titled compound. MW: 298.35; mp: 117.0–118.0° C.; $^1$H-NMR (CDCl$_3$) δ: 8.91 (1H, d, J=1.5 Hz), 8.78–8.74 (2H, m), 8.05 (1H, d, J=16.1 Hz), 7.88–7.84 (1H, m), 7.55–7.49 (3H, m), 7.42–7.28 (5H, m), 7.12 (1H, d, J=16.1 Hz).

Example 20

(E)-2-Styryl-1-(2-thiazolyl)-1H-benzimidazole

A stirred mixture of 2-styryl-1H-benzimidazole (220 mg, 1 mmol), 2-bromothiazole (328 mg, 2 mmol), potassium carbonate (138 mg, 1 mmol), copper bronze (20 mg) and nitrobenzene (10 ml) was heated to reflux under a nitrogen atmosphere for 7 h. The cooled reaction mixture was diluted with ethyl acetate (150 ml) and filtered through a pad of celite. The filtrate was washed consecutively with water (50 ml), and brine (50 ml), dried (magnesium sulfate) and concentrated to dryness. Column chromatography (silica gel, 100 g; n-hexane/ethyl acetate (9/1 to 3/1)) gave 199 mg of the titled compound as an orange oil, which was solidified on standing at room temperature. Recrystallization from isopropyl ether gave 117 mg (39%) of the titled compound as colorless crystals. MW: 303.39; mp: 99.0–99.5° C.; $^1$H-NMR (CDCl$_3$) δ: 8.01 (1H. d, J=15.8 Hz), 7.91 (1H, d, J=3.7 Hz), 7.85–7.80 (1H, m), 7.69–7.64 (1H, m), 7.59–7.54 (2H, m), 7.51 (1H, d, J=3.7 Hz), 7.40 (1H, d, J=15.8 Hz), 7.42–7.29 (5H, m).

Example 21

(E)-2-(2-Methylstyryl)-1-(2-pyridyl)-1H-benzimidazole hydrochloride

Free base of the titled compound was prepared from N-(2-pyridyl)-o-phenylenediamine and (E)-2-methylcinnamoyl chloride (Sekiya, T.; Hiranuma, H.; Hata, S.; Mizogami, S.; Hanazuka, M.; Yamada, S. *J. Med. Chem.,* 1983, 26, 411) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 347.85; mp: 212.0–215.0° C.; $^1$H-NMR (CDCl$_3$) δ: 9.26 (1H, d, J=16.1 Hz), 8.89–8.83 (1H, m), 8.24–8.12 (2H, m), 7.72–7.64 (2H, m), 7.59–7.43 (4H, m), 7.43–7.11 (3H, m), 6.92 (1H, d, J=16.1 Hz), 2.70 (3H, s).

Example 22

(E)-2-(2-Fluorostyryl)-1-(2-pyridyl)-1H-benzimidazole hydrochloride

Free base of the titled compound was prepared from N-(2-pyridyl)-o-phenylenediamine and (E)-2- fluorocinnamoyl chloride (Amino, Y.; Kawada, K.; Toi, K.; Kumashiro, I.; Fukushima, K. *Chem. Pharm. Bull,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 351.81; mp: 226.0–228.0° C.; $^1$H-NMR (DMSO) δ: 8.92–8.87 (1H, m), 8.39–8.29 (1H, m), 8.29 (1H, d, J=16.1 Hz), 7.99–7.79 (4H, m), 7.70–7.51 (4H, m), 7.44–7.31 (3H, m).

Example 23

(E)-2-(2–Chlorostyryl)-1-(2-pyridyl-1H-benzimidazole hydrochloride

Free base of the titled compound was prepared from N-(2-pyridyl)-o-phenylenediamine and (E)-2–Chlorocinnamoyl chloride (Amino, Y.; Kawada, K.; Toi, K; Kumashiro, I.; Fukushima, K. *Chem. Pharm Bull.,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 368.27; mp: 225.0–229.0° C.; $^1$H-NMR (DMSO) δ: 8.83–8.76 (1H, m), 8.28 (1H, d, J=16.1 Hz). 8.27–8.19 (1H, m), 7.90–7.80 (3H, m), 7.75–7.68 (1H, m), 7.59–7.34 (6H, m), 7.28 (1H, d, J=16.1 Hz).

Example 24

(E)-2-Methoxystyryl-1-(2-pyridyl)-1H-benzimidazole oxalate

Free base of the titled compound was prepared from N-(2-pyridyl)-o-phenylenediamine and 2-methoxycinnamoyl chloride (Vallaerda, J.; Appelberg, U.; Csoeregh, I.; Hacksell, U. *J. Chem. Soc. Perkin Trans. I;* 1994, 17, 461) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 417.42; mp: 123.0–125.0° C.; $^1$H-NMR (DMSO) δ: 8.81–8.77 (1H, m), 8.20 (1H, td, J=7.7,2.0 Hz), 8.10 (1H, d, J=16.1 Hz), 7.75 (2H, dd, J=8.1, 1.1 Hz), 7.68–7.62 (1H, m), 7.57 (1H, dd, J=7.7, 1.5 Hz), 7.46–7.42 (1H, m), 7.39–7.23 (4H, m) 7.08 (1H, d, J=7.7 Hz), 6.97 (1H, t, J=7.3 Hz), 3.86 (3H, s).

Example 25

(E)-2-(2,4-Difluorostyryl)-1-(2-pyridyl)-1H-benzimidazole hydrochloride

To a solution of (E)-2,4-difluorocinnamic acid (331 mg, 1.8 mmol) in benzene (10 ml) was added thionyl chloride (0.5 ml) and the mixture was heated to reflux for 60 min. Volatiles were removed by evaporation to give crude (E)-2,4-difluorocinnamoyl chloride. Free base of the titled compound was prepared from N-(2-pyridyl)-o-phenylenediamine (250 mg, 1.4 mmol) and (E)-2,4-difluorocinnamoyl chloride obtained as above according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 369.80; mp: 194.8–196.8° C.; $^1$H-NMR (DMSO) δ: 8.84–8.79 (1H, m), 8.30–8.08 (2H, m), 7.96–7.82 (3H, m), 7.78–7.69 (1H, m), 7.61–7.13 (6H, m).

Example 26

(E)-2-(2.6-Difluorostyryl)-1-(2-pyridyl)-1H-benzimidazole hydrochloride

To a solution of (E)-2,6-difluorocinnamic acid (331 mg, 1.8 mmol) in benzene (10 ml) was added thionyl chloride (0.5 ml) and the mixture was heated to reflux for 60 min. Volatiles were removed by evaporation to give crude (E)-2,6-difluorocinnamoyl chloride. Free base of the titled compound was prepared from N-(2-pyridyl)-o-phenylenediamine (250 mg, 1.4 mmol) and (E)-2,6-difluorocinnamoyl chloride obtained as above according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 369.80; mp: 204.5–206.5° C.; $^1$H-NMR (DMSO) δ: 8.82–8.77 (1H, m), 8.29–8.18 (1H, m), 8.00 (1H, d, J=16.5 Hz), 7.89–7.80 (2H, m), 7.74–7.66 (1H, m), 7.58–7.34 (4H, m), 7.39 (1H, d, J=16.5 Hz), 7.27–7.16 (2H, m).

Example 27

(E)-2-(3-Methylstyryl)-1-(2-pyridyl)-1H-benzimidazole hydrochloride

Free base of the titled compound was prepared from N-(2-pyridyl)-o-phenylenediamine and (E)-3-methylcinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from 2-propanol/isopropyl ether yielded the titled compound. MW: 347.85; mp: 213.0–235.0° C.; $^1$H-NMR (DMSO) δ: 8.87–8.82 (1H, m), 8.33–8.20 (2H, m), 7.89 (2H, d, J=8.1 Hz), 7.81–7.74 (1H, m), 7.63–7.45 (5H, m), 7.40–7.24 (2H, m), 7.19 (1H, d, J=16.5 Hz), 2.35 (3H, s).

Example 28

(E)-2-(3-Trifluoromethylstyryl)-1-(2-pyridyl)-1H-benzimidazole hydrochloride

Free base of the titled compound was prepared from N-(2-pyridyl)-o-phenylenediamine and (E)-3-trifluoromethylcinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethanol yielded the titled compound. MW: 401.82; mp:>230° C.; $^1$H-NMR (DMSO) δ: 8.83–8.77 (1H, m), 8.14–8.06 (1H, m), 7.81(1H, d, J=7.7 Hz), 7.67 (1H, dd, J=7.3,4.8 Hz), 7.56–7.22 (10H, m).

Example 29

(E)-2-(3-Fluorostyryl)-1-(2-pyridyl)-1H-benzimidazole

The titled compound was prepared from N-(2-pyridyl)-o-phenylenediamine and (E)-3-fluorocinnamoyl chloride (Nishikawa, Y.; Shindo, T.; Ishii, K.; Nakamura, H.; Kon, T.; Uno, H. *Chem. Pharm. Bull.,* 1989, 37, 100) according to the preparation of (E)-1-(2-pyridyl)-2-styryl-1H-benzimidazole (Example 1, method A). MW: 315.35; mp: 139.5–140.5° C.; $^1$H-NMR (CDCl$_3$) δ: 8.80–8.75 (1H, m), 8.05–7.96 (1H, m), 7.96 (1H, d, J=16.1 Hz), 7.87–7.80 (1H, m), 7.53–7.42 (3H, m), 7.39–7.14 (5H, m), 7.16 (1H, d, J=16.1 Hz), 7.05–6.94 (1H, m).

Example 30

(E)-2-(3–Chlorostyryl)-1-(2-pyridyl)-1H-benzimidazole hydrochloride

Free base of the titled compound was prepared from N-(2-pyridyl)-o-phenylenediamine and (E)-3–Chlorocinnamoyl chloride (Amino, Y.; Kawada, K.; Toi, K.; Kumashiro, I.; Fukushima, K. *Chem. Pharm. Bull,* 1988, 36, 4426) according to the preparation of (E)-1-(2-pyridyl)-2-styryl-H-benzimidazole (Example 1, method A). The free base was dissolved with a 10% methanol solution of hydrogen chloride (5 ml). Concentration and recrystallization from ethyl acetate/ethanol yielded the titled compound. MW: 368.27; mp:>230° C.; $^1$H-NMR (DMSO) δ: 8.85–8.81 (1H, m), 8.31–8.22 (1H, m), 8.20 (1H, d, J=16.1 Hz), 7.90–7.81 (3H, m), 7.78–7.72 (1H, m), 7.68–7.43 (6H, m), 7.33 (1H, d, J=16.1 Hz).

Example 31

(E)-3-Methoxystyryl-1-(2-pyridyl)-1H-benzimidazole oxalate

Free base of the titled compound was prepared from N-(2-pyridyl)-o-phenylenediamine and 3-methoxycinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 417.42; mp: 163.0–164.0° C.; $^1$H-NMR (DMSO) δ: 8.78 (1H, dd, J=4.9, 1.3 Hz), 8.19 (1H, td, J=7.9, 2.0 Hz), 7.87 (1H, d, J=15.8 Hz), 7.77–7.72 (2H, m), 7.67–7.61 (1H, m), 7.48–7.44 (1H, m), 7.36–7.24 (3H, m), 7.22–7.15 (3H, m), 6.96–6.92 (1H, m), 3.78 (3H, s).

Example 32

(E)-2-(3-Hydroxystytryl)-1-(2-pyridyl)-1H-benzimidazole oxalate

According to the literature procedure (Kawasaki, I.; Matsuda, K.; Kaneko, T. *Bull. Chem. Soc. Jpn.* 1971, 44, 1986.), a solution of (E)-2-(3-methoxystyryl)-1-(2-pyridyl)-1H-benzimidazole (76 mg, 0.23 mmol), glacial acetic acid (10 ml) and 48% aqueous solution of hydrogen bromide (5 ml) was heated under reflux condition for 4 h. The resulting solution was neutralized by sodium hydroxide pellet and this mixture was extracted with dichloromethane (3×15 ml). Combined organic layer was dried (magnesium sulfate) and filtered. The filtrate was concentrated then the residue (39 mg, 54%) and oxalic acid (12 mg, 0.12 mmol) were dissolved into ethyl acetate. Concentration and recrystallization from ethyl acetate/n-hexane yielded the titled compound. MW: 403.40; mp: 188.0–189.0° C.; $^1$H-NMR (DMSO) δ: 8.80–8.77 (1H, m), 8.20 (1H, td, J=8.1, 1.8 Hz), 7.79 (1H, d, J=16.1 Hz), 7.78–7.72 (2H, m), 7.68–7.62 (1H, m), 7.46–7.42 (1H, m), 7.36–7.16 (4H, m), 7.07 (1H, d, J=16.1 Hz), 7.05–6.95 (2H, m), 6.78–6.74 (1H, m).

Example 33

(E)-3 4-Dimethoxystyryl-1-(2-pyridyl)-1H-benzimidazole oxalate

Free base of the titled compound was prepared from N-(2-pyridyl)-o-phenylenediamine and 3,4-dimethoxycinnamoyl chloride (Ramamurthy, B.; Sugumaran, M. *Synthesis,* 1987, 523) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 447.45; mp: 178.0–179.0° C.; $^1$H-NMR (DMSO) δ: 8.79–8.76 (1H, m), 8.18 (1H, td, J=7.7, 1.8 Hz), 7.83 (1H, d, J=16.1 Hz), 7.72 (2H, d, J=6.8 Hz), 7.63 (1H, dd, J=7.5, 5.0 Hz), 7.44 (1H, d, J=7.3 Hz), 7.34–7.15 (4H, m), 7.04 (1H, d, J=16.1 Hz), 6.99 (1H, t, J=8.1 Hz), 3.78 (6H, s).

Example 34

(E)-1-(2-Pyridyl)-2-(4-methylstyryl)-1H-benzimidazole hydrochloride

Free base of the titled compound was prepared from N-(2-pyridyl)-o-phenylenediamine and (E)-4-methylcinnamoyl chloride (Aitken, R. A.; Boeters, C.; Morrison, J. J. *J. Chem. Soc. Perkin Trans.I;* 1994, 17, 2473) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 347.85; mp:>220° C.; $^1$H-NMR (CDCl$_3$) δ: 9.04 (1H, d, J=16.1 Hz), 8.89–8.84 (1H, m), 8.17 (2H, d, J=7.7 Hz), 7.72–7.66 (2H, m), 7.58–7.42 (5H, m), 7.17 (2H, d, J=7.7 Hz), 6.91 (1H, d, J=16.1 Hz), 2.35 (3H, s).

Example 35

(E)-2-(4-Ethylstyryl-1-(2-pyridyl)-1H-benzimidazole hydrochloride

Free base of the titled compound was prepared from N-(2-pyridyl)-o-phenylenediamine and (E)-4-ethylcinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml).

Concentration and recrystallization from ethyl acetate/ethanol yielded the titled compound. MW: 361.88; mp: 197.2–198.8° C.; $^1$H-NMR (DMSO) δ: 8.93–8.88 (1H, m), 8.39–8.30 (1H, m), 8.23 (1H, d, J=16.1 Hz), 7.95 (2H, d, J=7.7 Hz), 7.88–7.78 (1H, m), 7.62–7.51 (5H, m), 7.38 (2H, d, J=7.7 Hz), 7.22 (1H, d, J=16.1 Hz), 2.72 (2H, q, J=7.7 Hz), 1.26 (3H, t, J=7.7 Hz).

Example 36

(E)-4-Isopropylstyryl-1-(2-pyridyl)-1H-benzimidazole oxalate

Free base of the titled compound was prepared from N-(2-pyridyl)-o-phenylenediamine and 4-isopropylcinnamoyl chloride (Perkin, W. H. *J. Chem. Soc.,* 1877, 31, 388) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 429.48; mp: 136.0–137.0° C.; $^1$H-NMR (DMSO) δ: 8.80–8.77 (1H, m), 8.19 (1H, td, J=7.9, 1.8 Hz), 7.86 (1H, d, J=16.1 Hz), 7.77–7.72 (2H, m), 7.67–7.61 (1H, m), 7.53 (2H, d, J=8.1 Hz), 7.47–7.43 (1H, m), 7.36–7.24 (2H, m), 7.27 (2H, d, J=8.4 Hz), 7.12 (1H, d, J=16.1 Hz), 2.52–2.49 (1H, m), 1.20 (6H, d, J=6.6 Hz).

Example 37

(E)-1-(2-Pyridyl)-2-(4-fluorostyryl)-1H-benzimidazole hydrochloride

Free base of the titled compound was prepared from N-(2-pyridyl)-o-phenylenediamine and (E)-4-fluorocinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 351.81; mp:>230° C.; $^1$H-NMR (CDCl$_3$) δ: 9.10 (1H, d, J=16.5 Hz), 8.89–8.84 (1H, m), 8.24–8.12 (2H, m), 7.72–7.43 (6H, m), 7.07 (2H, dd, J=8.4, 8.4 Hz), 6.91 (1H, d, J=16.5 Hz), 6.82 (1H, dd, J=8.8, 8.8 Hz).

Example 38

(E)-1-(2-Pyridyl)-2-(4-methoxystyryl)-1H-benzimidazole

The titled compound was prepared from N-(2-pyridyl)-o-phenylenediamine and (E)-3-methoxycinnamoyl chloride (Wiesler, W. T.; Nakanishi, K. *J. Am. Chem. Soc.,* 1990, 112, 5574) according to the preparation of (E)-1-(2-pyridyl)-2-styryl-1H-benzimidazole (Example 1, method A). MW: 327.39; mp: 145.5–146.5° C.; $^1$H-NMR (CDCl$_3$) δ: 8.81–8.76 (1H, m), 8.04–7.96 (1H, m), 7.98 (1H, d, J=16.1 Hz), 7.85–7.79 (1H, m), 7.56–7.41 (5H, m), 7.37–7.22 (3H, m), 7.00 (1H, d, J=16.1 Hz), 6.88 (1H, d, J=8.4 Hz), 3.83 (3H, s).

Example 39

(E)-4-Ethoxylstyryl-1-(2-pyridyl)-1H-benzimidazole oxalate

Free base of the titled compound was prepared from N-(2-pyridyl)-o-phenylenediamine and 4-ethoxycinnamoyl chloride (Lohar, J. M.; Mahsru, U. *Indian J. Chem. Sect. A,* 1981, 20, 125) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 431.45; mp: 169.0–170.0° C.; $^1$H-NMR (DMSO) δ: 8.78 (1H, dd, J=5.1, 1.4 Hz), 8.18 (1H, td, J=7.7, 1.8 Hz), 7.85 (1H, d, J=16.1 Hz), 7.73 (2H, t, J=6.8 Hz), 7.67–7.61 (1H, m), 7.55 (2H, d, J=8.8 Hz), 7.43 (1H, d, J=7.7 Hz), 7.35–7.22 (2H, m), 7.01 (1H, d, J=16.1 Hz), 6.94 (2H, d, J=8.8 Hz), 4.06 (2H, q, J=7.0 Hz), 1.33 (3H, t, J=7.0 Hz).

Example 40

(E)-1-(2-Pyridyl)-2-(4-methylthiostyryl)-1H-benzimidazole

The titled compound was prepared from N-(2-pyridyl)-o-phenylenediamine and (E)-3-methylthiocinnamoyl chloride (Miller, R. D.; Reiser, O. *J. Heterocycl. Chem.* 1993, 30, 755) according to the preparation of (E)-1-(2-pyridyl)-2-styryl-1H-benzimidazole (Example 1, method A). MW: 343.46; mp: 139.6–140.6° C.; $^1$H-NMR (CDCl$_3$) δ: 8.78 (1H, dd, J=5.1, 2.2 Hz), 8.00 (1H, ddd, J=7.7, 7.7, 2.2 Hz), 7.96 (1H, d, J=16.1 Hz), 7.83 (1H, d, J=7.3 Hz), 7.54–7.39 (5H, m), 7.38–7.18 (4H, m), 7.10 (1H, d, J=16.1 Hz), 2.49 (3H, s).

Example 41

(E)-2-(3-Methyl-1-butenyl)-1-(2-pyridyl)-1H-benzimidazole hydrochloride

Free base of the titled compound was prepared from N-(2-pyridyl)-o-phenylenediamine and 4-methyl-2-pentenoyl chloride (Yamada, T.; Takashima, K.; Miyazawa, T.; Kuwata, S.; Watanabe, H. *Bull. Chem. Soc. Jpn.* 1978, 51, 878) according to the preparation of (E)-1-(2-pyridyl)-2-styryl-1H-benzimidazole (Example 1, method A). The free base was treated with a 10% methanol solution of hydrogen chloride and concentrated to dryness. The residue was recrystallized from ethyl acetate-hexane to give the titled compound. MW: 299.81; mp: 140.0–141.0° C.; $^1$H-NMR (DMSO) δ: 8.81–8.79 (1H, m), 8.25 (1H, td, J=8.1, 1.8 Hz), 7.85–7.79 (2H, m), 7.77–7.71 (1H, m), 7.56–7.45 (3H, m), 7.31 (1H, dd, J=16.1, 7.0 Hz), 6.47–6.40 (1H, m), 2.75–2.55 (1H, m), 1.05 (6H, d, J=7.0 Hz).

Example 42

(E)-2-(3.3-Dimethyl-1-butenyl)-1-(2-pyridyl)-1H-benzimidazole hydrochloride

To a solution of (E)-4,4-dimethyl-2-pentenoic acid (Gream, G. E.; Serelis, A. K. *Aust. J. Chem.* 1978, 31, 863) (200 mg, 1.6 mmol) in benzene (10 ml) was added thionyl chloride (0.5 ml) and the mixture was heated to reflux for 60 min. Volatiles were removed by evaporation to give crude (E)-4,4-dimethyl-2-pentenoyl chloride. Free base of the titled compound was prepared from N-(2-pyridyl)-o-phenylenediamine (150 mg, 0.81 mmol) and (E)-4,4-dimethyl-2-pentenoyl chloride obtained as above according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate yielded the titled compound. MW: 313.83; mp: 171.0–172.3° C.; $^1$H-NMR (CDCl$_3$) δ: 8.86–8.82 (1H, m), 8.27 (1H, d, J=16.3 Hz), 8.21–8.13 (2H, m), 7.72–7.65 (1H, m), 7.62–7.43 (4H, m), 6.31 (1H, d, J=16.3 Hz), 1.17 (9H, s).

Example 43

(E)-2-[2-(Cyclohexyl)ethenyl]-1-(2-pyridyl)-1H-benzimidazole

The titled compound was prepared from N-(2-pyridyl)-o-phenylenediamine and (E)-3–Cyclohexylacryloyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). MW: 303.41; mp: 105.0–106.0° C.; $^1$H-NMR (CDCl$_3$) δ: 8.78–8.73 (1H, m), 7.96 (1H, ddd, J=7.7, 7.7, 1.8 Hz), 7.81–7.76 (1H, m), 7.49–7.39 (3H, m), 7.33–7.18 (2H, m), 7.11 (1H, dd, J=15.8, 7.3 Hz), 6.42 (1H, dd, J=15.8, 1.5 Hz), 2.26–2.12 (1H, m), 1.98–1.60 (5H, m), 1.39–1.10 (5H, m).

Example 44

(E)-1-(2-Pyridyl)-2-[2-(2-pyridyl)ethenyl]-1H-benzimidazole dihydrochloride 1. 2-Methyl-1-(2-pyridyl)-1H-benzimidazole To a stirred solution of 2-methyl-1H-benzimidazole (6.61 g, 50 mmol) in dimethylacetamide (40 ml) at room temperature under a nitrogen atmosphere was added sodium hydride (2.40 g, 60 mmol) in portions during 15 min. At the point where the reaction mixture was too viscous to stir, the reaction was diluted with 100 ml of dimethylacetamide. After 50 min., a solution of 2-fluoropyridine (5.83 g, 60 mmol) in dimethylacetamide (30 ml) was added during 15 min. The resulting mixture was heated at 100° C. for 2 h and then to reflux for about 4 h. Volatiles were removed by evaporation under reduced pressure. The residue was dissolved into ethyl acetate (200 ml) and washed consecutively with water (3×100 ml) and brine (100 ml). The organic layer was dried (magnesium sulfate) and concentrated to dryness. Purification by column chromatography (silica gel, 300 g; n-hexane/ethyl acetate (17/3)) yielded 7.46 g (71%) of the titled compound as a light yellow liquid. $^1$H-NMR (CDCl$_3$) δ: 8.72–8.67 (1H, m), 7.95 (1H, ddd, J=7.7, 7.7, 1.8 Hz), 7.78–7.74 (1H, m), 7.49–7.36 (3H, m), 7.32–7.20 (2H, m), 2.69 (3H, s).

2. (E)-1-(2-Pyridyl)-2-[2-(2-pyridyl)ethenyl]-1H-benzimidazole dihydrochloride

A stirred mixture of 2-methyl-1-(2-pyridyl)-1H-benzimidazole (0.50 g, 2.39), pyridine-2-carboxaldehyde (0.50 g, 4.67 mmol) and acetic anhydride (5 ml) was heated to 80° C. for 1.5 h and then to reflux for about 6 h. After cooling, the mixture was diluted with water (15 ml), basified with a 10% aqueous solution of sodium hydroxide (100 ml) and extracted with dichloromethane (2×100 ml). The combined organic layers were washed with water (100 ml) and extracted with 2 N hydrochloric acid (3×50 ml). The combined aqueous extracts were basified with a 50% aqueous solution of sodium hydroxide (3×50 ml) and extracted with dichloromethane (4×50 ml). The combined organic extracts were washed consecutively with water (100 ml) and brine (100 ml), dried (magnesium sulfate) and concentrated to dryness. Column chromatography (silica gel, 125 g; ethyl acetate) gave 0.18 g of free base (E)-1-(2-pyridyl)-2-[2-(2-pyridyl)ethenyl]-1H-benzimidazole as a brown oil. This product was dissolved into methanol (5 ml), treated with a 10% methanol solution of hydrogen chloride (5 ml) and concentrated to dryness. Recrystallization from 2-propanol afforded 0.15 g (21%) of the titled compound. MW: 371.27; mp: 148.0–155.0° C.; $^1$H-NMR (DMSO-$_6$) δ: 8.84–8.78 (1H, m), 8.74–8.69 (1H, m), 8.30–8.22 (1H, m), 8.19–8.10 (2H, m), 8.02–7.95 (1H, m), 7.91–7.84 (2H, m), 7.79–7.70 (2H, m), 7.65–7.40 (4H, m).

Example 45

(E)-2-[2-(2-Furyl)ethenyl]-1-(2-pyridyl)-1H-benzimidazole

The titled compound was prepared from N-(2-pyridyl)-o-phenylenediamine and (E)-3-(2-furyl)acryloyl chloride (New, J. S.; Christopher, W. L.; Yevich, J. P.; Butler, R.; Schlemmer, R. F.; VanderMaelen, C. P.; Cipollina, J. A. *J. Med. Chem.*, 1989, 32, 1147) according to the preparation of (E)-1-(2-pyridyl)-2-styryl-1H-benzimidazole (Example 1, method A). MW: 287.32; mp: 164.0–165.0° C.; $^1$H-NMR (CDCl$_3$) δ: 8.80–8.75 (1H, m), 8.00 (1H, ddd, J=7.7, 7.7, 1.8 Hz), 7.83–7.78 (1H, m), 7.78 (1H, d, J=15.4 Hz), 7.54–7.39 (4H, m), 7.37–7.16 (2H, m), 7.01 (1H, d, J=15.4 Hz), 6.51 (1H, d, J=3.3 Hz), 6.44 (1H, dd, J=3.3, 1.8 Hz).

Example 46

(E)-2-[2-(3-Furyl)ethenyl]-1-(2-pyridyl)-1H-benzimidazole

The titled compound was prepared from N-(2-pyridyl)-o-phenylenediamine and (E)-3-(3-furyl)acryloyl chloride (Shizuri, Y.; Ojika, M.; Yamada, K. *Tetrahedron Lett.*, 1981, 22, 4291) according to the preparation of (E)-1-(2-pyridyl)-2-styryl-1H-benzimidazole (Example 1, method A). MW: 287.32; mp: 162.5–164.0° C.; $^1$H-NMR (CDCl$_3$) δ: 8.79–8.75 (1H, m), 7.99 (1H ddd, J=7.7, 7.7, 1.8 Hz), 7.87 (1H, d, J=15.8 Hz), 7.83–7.78 (1H, m), 7.64–7.62 (1H, m), 7.53–7.39 (4H, m), 7.37–7.22 (2H, m), 6.85 (1H, d, J=15.8 Hz), 6.55 (1H, d, J=1.8 Hz).

Example 47

(E)-2-[2-(3-Furyl)ethenyl]-1-(4-pyridyl)-1H-benzimidazole

The titled compound was prepared from N-(4-pyridyl)-o-phenylenediamine and (E)-3-(3-furyl)acryloyl chloride according to the preparation of (E)-1-(4-pyridyl)-2-styryl-1H-benzimidazole (Example 3). MW: 287.32; mp: 171.5–172.5° C.; $^1$H-NMR (DMSO) δ: 8.88 (2H, dd, J=4.6, 1.7 Hz), 8.07 (1H, br.s), 7.81 (1H, d, J=15.8 Hz), 7.74–7.65 (4H, m), 7.35–7.25 (3H, m), 6.89 (1H, br.s), 6.73 (1H, d, J=15.8 Hz).

Example 48

(E)-1-(2-Pyridyl)-2-[2-(2-thienyl)ethenyl]-1H-benzimidazole

The tilled compound was prepared from N-(2-pyridyl)-o-phenylenediamine and (E)-3-(2-thienyl)acryloyl chloride (Aitken, R. A.; Boeters, C.; Morrison, J. J. *J. Chem. Soc. Perkin. Trans.* 1, 1994, 17, 2473) according to the preparation of (E)-1-(2-pyridyl)-2-styryl-1H-benzimidazole (Example 1, method A). MW: 303.39; mp: 130.0–131.0° C.; $^1$H-NMR (CDCl$_3$) δ: 8.77 (1H, ddd, J=4.8, 1.8, 0.7 Hz), 8.12 (1H, d, J=15.8 Hz), 8.02 (1H, ddd, J=8.1,8.1, 1.8 Hz), 7.84–7.79 (1H, m), 7.51 (1H, ddd, J=8.1, 1.1, 0.7 Hz), 7.49–7.43 (2H, m), 7.37–7.18 (3H, m), 7.20 (1H, dd, J=3.7, 0.7 Hz), 7.02 (1H, dd, J=4.8, 3.7 Hz), 6.94 (1H, d, J=15.8 Hz).

Example 49

(E)-1-(2-Pyridyl)-2-[2-(3-thienyl)ethenyl]-1H-benzimidazole

The titled compound was prepared from N-(2-pyridyl)-o-phenylenediamine and (E)-3-(3-thienyl)acryloyl chloride (New, J. S.; Christopher, W. L.; Yevich, J. P.; Butler, R.; Schlemmer, R. F.; VanderMaelen, C. P.; Cipollina, J. A. *J. Med. Chem*, 1989, 32, 1147) according to the preparation of (E)-1-(2-pyridyl)-2-styryl-1H-benzimidazole (Example 1, method A). MW: 303.39; mp: 135.5–136.0° C.; $^1$H-NMR (CDCl$_3$) δ: 8.77 (1H, ddd, J=5.1, 1.8, 0.7 Hz), 8.03–7.95 (2H, m), 7.84–7.80 (1H, m), 7.54–7.43 (4H, m), 7.38–7.24 (4H, m), 6.97 (1H, d, J=15.7 Hz).

Example 50

(E)-2-[2-(2.5-Dimethyl-3-thienyl)ethenyl]-1-(2-pyridyl)-1H-benzimidazole hydrochloride To a solution of (E)-3-(2,5-dimethylthiophene-3-yl) acrylic acid (328 mg, 1.8 mmol) in benzene (10 ml) was added thionyl chloride (0.5 ml) and the mixture was heated to reflux for 60 min. Volatiles were removed by evaporation to give crude (E)-3-(2,5-dimethylthiophene-3-yl)acryloyl chloride. Free base of the titled compound was prepared from N-(2-pyridyl)-o-phenylenediamine (250 mg, 1.4 mmol) and (E)-3-(2,5-dimethylthiophene-3-yl)acryloyl chloride obtained as above according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 367.91; mp:>230° C.; $^1$H-NMR (CDCl$_3$) δ: 8.98–8.83 (2H, m), 8.25–8.16 (1H, m), 8.10–8.02 (1H, m), 7.76–7.68 (2H, m), 7.60–7.42 (3H, m), 6.78–6.73 (1H, m), 6.61 (1H, d, J=16.1 Hz), 2.75 (3H, s), 2.38 (3H, s).

Example 51

(E)-2-(2.2-Diphenylethenyl)-1-(2-pyridyl)-1H-benzimidazole oxalate

Free base of the titled compound was prepared from N-(2-pyridyl)-o-phenylenediamine and 2-phenylcinnamoyl chloride (Haynes, 3. K.; Kampmeier, J. A. *J. Org. Chem.,* 1972, 25, 4167) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 463.50; mp: 160.0–161.0° C.; $^1$H-NMR (DMSO) δ: 8.55–8.51 (1H, m), 7.96 (1H, td, J=7.7, 1.8 Hz), 7.61–7.57 (1H, m), 7.49 (1H, d, J=8.1 Hz), 7.46–7.36 (5H, m), 7.29–7.22 (5H, m), 7.19–7.13 (2H, m), 6.96 (1H, s), 6.81 (2H, d, J=7.0 Hz).

Example 52

(E)-2-(2-Methyl-2-phenyllethenyl)-1-(2-pyridyl)-1H-benzimidazole oxalate

Free base of the titled compound was prepared from N-(2-pyridyl)-o-phenylenediamine and (E)-β-methylcinnamoyl chloride (Balsamo, A.; Crotti, P.; Lapucci, A.; Macchia, B.; Macchia, F. *J. Med. Chem.,* 1981, 24, 525) according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 446.44; mp: 92.0–94.0° C.; $^1$H-NMR (DMSO) δ: 8.77–8.74 (1H, m), 8.16 (1H, td, J=7.7, 2.1 Hz), 7.81–7.77 (1H, m), 7.73 (1H, d, J=8.1 Hz), 7.64–7.58 (1H, m), 7.52–7.48 (2H, m), 7.45–7.27 (6H, m), 6.70 (1H, d, J=1.5 Hz), 2.76 (3H, d, J=1.5 Hz).

Example 53

(Z)-2-(1-Fluoro-2-phenylethenyl)-1-(2-pyridyl)-1H-benzimidazole

The titled compound was prepared from N-(2-pyridyl)-o-phenylenediamine and (Z)-α-fluorocinnamoyl chloride (Amino, Y.; Kawada, K.; Toi, K.; Kumashiro, I.; Fukushima, K. *Chem. Pharm. Bull.,* 1988, 36, 4426) according to the preparation of (E)-1-(2-pyridyl)-2-styryl-1H-benzimidazole (Example 1, method A). MW: 315.35; mp: 124.5–125.3° C.; $^1$H-NMR (CDCl$_3$) δ: 8.72–8.66 (1H, m), 7.94 (1H, ddd, J=7.3, 7.3, 1.8 Hz), 7.88–7.83 (1H, m), 7.62–7.55 (2H, m), 7.52–7.25 (8H, m), 7.00 (1H, d, J=38.5 Hz).

Example 54

(E)-2-(2–Cyclohexlidenyl-1–Cyanoethenyl)-1-(2-pyridyl)-1H-benzimidazole oxalate

Free base of the titled compound was prepared from N-(2-pyridyl)-o-phenylenediamine and cyclohexylidene cyanoacetylchloride (Jaafar, I.; Francis, G.; Danion-Bougot, R.; Danion, D. *Synthesis,* 1994, 56) according to the preparation of (E)-1-(2-pyridyl)-2-styryl-1H-benzimidazole (Example 1, method A). The free base was treated with a 10% methanol solution of hydrogen chloride and concentrated to dryness. The residue was recrystallized from ethyl acetate/n-hexane to give the titled compound. MW: 387.31; mp: 182.0–184.0° C.; $^1$H-NMR (DMSO) δ: 8.85–8.69 (2H, m), 8.19–8.13 (1H, m), 7.82–7.57 (3H, m), 7.41–7.33 (2H, m), 2.60–2.54 (2H, m), 2.23–2.17 (2H, m), 1.80–1.15 (6H, m).

Example 55

(E)-2-(2-Methyl-1-propenyl)-1-(2-pyridyl)-1H-benzimidazole oxalate

Free base of the titled compound was prepared from N-(2-pyridyl)-o-phenylenediamine and 3-methyl-2-butenoyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 339.35; mp: 136.0–137.5° C.; $^1$H-NMR (DMSO) δ: 8.74 (1H, d, J=4.8 Hz), 8.14 (1H, t, J=7.7 Hz), 7.73–7.57 (3H, m), 7.35–7.19 (3H, m), 6.14 (1H, s), 2.32 (3H, s), 1.91 (3H, s).

Example 56

(E)-4-Methyl-1-(2-pyridyl)-2-styryl-1H-benzimidazole hydrochloride 1. (E)-4-Methyl-2-styryl-1H-benzimidazole A mixture of 2,3-diaminotoluene (2.44 g, 20 mmol), (E)-cinnamic acid (2.96 g, 20 mmol) and polyphosphoric acid (10 g) was heated to 180° C. for 90 min. The hot mixture was poured into water (100 ml), basified with 50% aqueous solution of sodium hydroxide and extracted with dichloromethane (3×100 ml). The combined extracts were washed with water (100 ml) and brine (100 ml), dried (magnesium sulfate) and concentrated to dryness. Purification by column chromatography (silica gel, 300 g; n-hexane/ethyl acetate (7/3)) yielded 0.61 g (13%) of the titled compound as red solids. $^1$H-NMR (CDCl$_3$) δ: 9.53 (1H, br.s), 8.72–8.67 (1H, m), 7.95 (1H ddd, J=7.7, 7.7, 1.8 Hz), 7.60–7.49 (3H, m), 7.43–7.31 (3H, m), 7.23–7.14 (3H, m), 7.09–7.04 (1H, m), 2.63 (3H, br.s)

2. (E)-4-Methyl-1-(2-pyridyl)-2-styryl-1H-benzimidazole hydrochloride

Free base of the titled compound was prepared from (E)-4-methyl-2-styryl-1H-benzimidazole and 2-fluoropyridine according to the preparation of (E)-1-(2-pyridyl)-2-styryl-1H-benzimidazole (Example 1, method B). The free base was treated with a 10% methanol solution of hydrogen chloride and concentrated to dryness. The residue was recrystallized from 2-propanol/isopropyl ether to give the titled compound. MW: 347.85; mp: 218.0–225.0° C.; $^1$H-NMR (DMSO) δ: 8.85–8.80 (1H, m), 8.45 (1H, d, J=16.1 Hz), 8.27 (1H, ddd, J=7.7,7.7, 1.5 Hz), 7.86 (1H, d, J=7.7 Hz), 7.77 (1H, dd, J=7.7, 4.5 Hz), 7.70–7.65 (2H, m), 7.48–7.42 (3H, m), 7.41–7.33 (3H, m), 7.17 (1H, d, J=16.1 Hz), 2.76 (3H, s).

Example 57

(E)-1-(2-Pyridyl)-2-styryl-5-trifluoromethyl-1H-benzimidazole 1. 2-Nitro-N-(2-pyridyl)-4-trifluoromethylaniline To a stirred suspension of sodium hydride (2.40 g, 60 mmol) in dimethylacetamide (60 ml) at room temperature under a nitrogen atmosphere was added a solution of 2-nitro-4-trifluoromethylaniline (10.31 g, 50 mmol) in dimethylacetamide (20 ml) during 30 min. After stirring the mixture at room temperature for 15 min., a solution of 2-fluoropyridine (5.83 g, 60 mmol) in dimethylacetamide (20 ml) was added during 5 min. The resulting mixture was heated to reflux for about 8 h. Volatiles were removed by evaporation under reduced pressure. The residue was dissolved into ethyl acetate (200 ml) and washed with water (3×100 ml). The organic layer was dried (magnesium sulfate) and concentrated to dryness. Column chromatography (silica gel, 250 g; n-hexane/ethyl acetate (17/3)) yielded 3.38 g (23%) of the titled compound as yellow solids. 1 H-NMR (CDCl$_3$) δ: 10.41 (1H, br.s), 9.02 (1H, d, J=9.2 Hz), 8.55–8.52 (1H, m), 8.42–8.38 (1H, m), 7.79–7.65 (2H, m), 7.05 (1H, dd, J=6.6, 4.8 Hz), 7.00 (1H, d, J=9.2 Hz).

2. 2-Amino-N-(2-pyridyl)-4-trifluoromethylaniline

A mixture of 2-nitro-N-(2-pyridyl)-4-trifluoromethylaniline (1.00 g, 3.5 mmol), 5% palladium on carbon (0.23 g) and methanol (50 ml) was stirred under a hydrogen atmosphere for 100 min. The mixture was filtered through a pad of celite and the filtrate was concentrated to dryness to give 0.75 g (85%) of the titled compound as yellow brown solids. $^1$H-NMR (CDCl$_3$) δ: 8.19 (1H, ddd, J=5.1, 1.8, 0.7 Hz), 7.49 (1H, ddd, J=8.3, 7.0, 1.8 Hz), 7.35 (1H, d, J=7.7 Hz), 7.05–7.01 (2H, m), 6.76 (1H, ddd, J=7.0, 5.1, 1.1 Hz), 6.55 (1H, ddd, J=8.3, 1.1, 0.7 Hz), 6.31 (1H, br.s), 3.98 (2H, br.s).

3. (E)-1-(2-Pyridyl)-2-styryl-5-trifluoromethyl-1H-benzimidazole

The titled compound was prepared from 2-amino-N-(2-pyridyl)-4-trifluoromethylaniline and (E)-cinnamoyl chloride according to the preparation of (E)-1-(2-pyridyl)-2-styryl-1H-benzimidazole (Example 1, method A). MW: 365.36; mp: 144.5–145.0° C.; $^1$H-NMR (CDCl$_3$) δ: 8.82–8.79 (1H, m), 8.12–8.00 (3H, m), 7.57–7.49 (6H, m), 7.41–7.31 (3H, m), 7.11 (1H, d, J=16.1 Hz).

Example 58

(E)-5-Methyl-1-(2-pyridyl)-2-styryl-1H-benzimidazole

The titled compound was prepared from 4-methyl-2-nitroaniline according to the preparation of (E)-1-(2-pyridyl)-2-styryl-5-trifluoromethyl-1H-benzimidazole (Example 57). MW: 311.39; mp: 144.8–146.0° C.; $^1$H-NMR (CDCl$_3$) δ: 8.77–8.72 (1H, m), 7.99–7.91 (1H, m), 7.98 (1H, d, J=16.1 Hz), 7.61 (1H, s), 7.53–7.26 (8H, m), 7.15 (1H, d, J=16.1 Hz), 7.10–7.05 (1H, m), 2.50 (3H, s).

Example 59

(E)-5-Fluoro-1-(2-pyridyl)-2-styryl-1H-benzimidazole

The titled compound was prepared from 4-fluoro-2-nitroaniline according to the preparation of (E)-1-(2-pyridyl)-2-styryl-5-trifluoromethyl-1H-benzimidazole (Example 57). MW: 315.35; mp: 134.0–135.0° C.; $^1$H-NMR (CDCl$_3$) δ: 8.78 (1H, ddd, J=4.8, 1.8, 1.1 Hz), 8.04–7.96 (1H, m), 8.00 (1H, d, J=15.8 Hz), 7.54–7.45 (5H, m), 7.42–7.30 (4H, m), 7.10 (1H, d, J=16.1 Hz), 7.01 (1H, td, J=9.2, 2.6 Hz).

Example 60

(E-5–Cyano-1-(2-peridyl)-2-styryl-1H-benzimidazole 1. 4–Cyano-2-nitro-N-(2-pyridyl)aniline A mixture of 4-Cyano-2-nitroaniline (10.8 g, 66 mmol), 2-bromopyridine (12.6 g, 80 mmol), anhydrous potassium carbonate (9.12 g, 66 mmol) and copper-bronze (1.0 g, 15.7 mmol) in nitrobenzene (100 ml) was heated overnight at 200° C. The reaction mixture was cooled and filtered through a pad of celite. The filter cake was washed with dichloromethane (500 ml) and the filtrate was evaporated. The resultant residue was purified by column chromatography (silica gel, 500 g; n-hexane/ethyl acetate/dichloromethane (4/1/1)) to afford 7.28 g (46%) of 4–Cyano-2-nitro-N-(2-pyridyl)aniline as orange solids. $^1$H-NMR (CDCl$_3$) δ: 10.53 (1H, br.s), 9.08 (1H, d, J=8.8 Hz), 8.58 (1H, d, J=8.8 Hz), 8.41 (1H, ddd, J=5.8, 1.8, 0.7 Hz), 7.78–7.69 (2H, m), 7.12–7.06 (1H, m), 7.02 (1H, d, J=8.8 Hz).

2. 2-Amino-4–Cyano-N-(2-pyridyl)aniline

4-Cyano-2-nitro-N-(2-pyridyl)aniline was converted to 2-amino-4-Cyano-N-(2-pyridyl)aniline according to the preparation of 2-amino-N-(2-pyridyl)-4-trifluoromethylaniline (Example 57). $^1$H-NMR (CDCl$_3$) δ: 8.19 (1H, dd, J=5.1, 1.1 Hz), 7.52 (1H, ddd, J=7.3, 7.3, 1.1 Hz), 7.45 (1H, d, J=8.4 Hz), 7.13–7.02 (3H, m), 6.78 (1H, ddd, J=7.3, 5.1, 1.1 Hz) 6.65 (1H, d, J=8.4 Hz), 3.99 (2H, br.s).

3. (E)-5-Cyano-1-(2-pyridyl)-2-styryl-1H-benzimidazole (E)-5-Cyano-1-(2-pyridyl)-2-styryl-1H-benzimidazole was prepared from 2-amino-4-Cyano-N-(2-pyridyl)aniline and (E)-cinnamoyl chloride according to the preparation of (E)-1-(2-pyridyl)-2-styryl-1H-benzimidazole (Example 1, method A). MW: 322.37; mp: 172.0–172.7° C.; $^1$H-NMR (CDCl$_3$) δ: 8.80 (1H. ddd, J=4.8, 1.8, 0.7 Hz), 8.15–8.02 (2H, m), 8.05 (1H, d, J=16.0 Hz), 7.57–7.48 (6H, m), 7.42–7.33 (3H, m), 7.07 (1H, d, J=16.0 Hz).

Example 61

(E)-5-Nitro-1-(2-pyridyl)-2-styryl-1H-benzimidazole

The titled compound was prepared from 2-(2-amino-4-nitroanilino)pyridine (Runti, C. Ann. Chim. (Rome), 1956, 46, 406) and (E)-cinnamoyl chloride according to the preparation of (E)-1-(2-pyridyl)-2-styryl-1H-benzimidazole (Example 1, method A). MW: 342.36; mp: 200.5–201.5° C.; $^1$H NMR (CDCl$_3$) δ: 8.82 (1H, ddd, J=4.8, 1.8, 0.7 Hz), 8.72 (1H, d, J=2.2 Hz), 8.20 (1H, dd, J=8.8, 2.2 Hz), 8.81 (1H, d, J=16.0 Hz), 8.66 (1H, ddd, J=8.1, 7.7, 1.8 Hz), 7.58–7.47 (5H, m), 7.45–7.32 (3H, m), 7.07 d, J=16.0 Hz).

Example 62

(E)-5-Amino-1-(2-pyridyl)-2-styryl-1H-benzimidazole

Iron powder (1.95 g, 35 mmol) and ammonium chloride (200 mg, 3.7 mmol) was added to a solution of (E)-5-nitro-1-(2-pyridyl)-2-styryl-1H-benzimidazole (2.41 g, 7.0 mmol) in ethanol (50 ml) and water (25 ml). After the reaction mixture was refluxed for 3 h, the hot reaction mixture was filtered through a pad of celite and the filtrate was evaporated under reduced pressure. The obtained residue was partitioned between ethyl acetate (200 ml) and saturated aqueous sodium bicarbonate solution (200 ml). The organic phase was separated and the aqueous phase was extracted with ethyl acetate (200 ml). The combined extracts were washed with brine (20 ml), dried (sodium sulfate) and concentrated in vacuo. The residue was purified by column chromatography (silica gel, 200 g; n-hexane/ethyl acetate (1/2)) and obtained solids (1.54 g, 70%) were recrystallized from ethyl acetate to afford the titled compound as brown solids. MW: 312.38; mp: 146.0–148.0° C.; $^1$H-NMR (CDCl$_3$) δ: 8.75 (1H, ddd, J=4.8, 1.8, 1.1 Hz), 8.01–7.91 (1H, m), 7.95 (1H, d, J=16.0 Hz), 7.56–7.23 (8H, m), 7.13 (1H, d, J=16.0 Hz), 7.11 (1H, d, J=2.2 Hz), 6.69 (1H, dd, J=8.8, 2.2 Hz), 3.70 (2H, br.s).

Example 63

(E)-5-Methylamino-1-(2-pyridyl-2-styryl-1H-benzimidazole hydrochloride

A mixture of (E)-5-amino-1-(2-pyridyl)-2-styryl-1H-benzimidazole (300 mg, 0.96 mmol) and triethyl orthoformate (3 ml) was refluxed with stirring for 6 h. Excess solvent was removed in vacuo and obtained solids were dissolved in ethanol (5 ml). Sodium borohydride (45 mg, 1.2 mmol) was added to this solution in one portion at 0° C. and the reaction mixture was stirred for 2 h at room temperature. The reaction mixture was poured into saturated aqueous sodium bicarbonate solution (50 ml) and the aqueous mixture was extracted with ethyl acetate (100 ml). The organic extract was washed consecutively with water (50 ml) and brine (50 ml), dried (sodium sulfate) and concentrated in vacuo. The residue was purified by column chromatography (silica gel, 100 g; n-hexane/ethyl acetate (1/1)) to give a brown oil. Then, it was dissolved with a 10% methanol solution of hydrogen chloride (5 ml). Volatiles were removed under reduced pressure and the residue was recrystallized from ethanol to afford 151 mg (43%) of the titled compound as yellow solids. MW: 373.80; mp: 170.8–172.5° C.; $^1$H-NMR (CDCl$_3$) δ: 8.89 (1H, d, J=16.5 Hz), 8.84–8.80 (1H, m), 8.13 (1H, ddd, J=7.7,7.7, 1.5 Hz), 7.67–7.57 (4H, m), 7.40–7.51 (3H, m), 7.24–7.16 (2H, m), 6.93 (1H, d, J=16.5 Hz), 6.80 (1H, dd, J=8.8,2.2 Hz), 2.92 (3H, s), 2.01 (1H, br.s).

Example 64

(E)-5-Dimethylamino-1-(2-pyridyl)-2-styryl-1H-benzimidazole

To a stirred solution of (E)-5-amino-1-(2-pyridyl)-2-styryl-1H-benzimidazole (355 mg, 1.1 mmol) in methanol (5 ml) was added methyl iodide (2 ml) and the reaction mixture was heated for 20 h at 50° C. The mixture was evaporated under reduced pressure and purified by column chromatography (silica gel, 100 g; n-hexane/ethyl acetate (1/1)). Recrystallization of the residue from ethyl acetate afforded 53 mg (14%) of the titled compound as brown solids. MW: 340.43; mp: 170.5–171.3° C.; $^1$H-NMR (CDCl$_3$) δ: 8.75 (1H, ddd, J=4.9, 1.8, 1.1 Hz), 7.97 (1H, d, J=15.8 Hz), 7.96 (1H, ddd, J=7.7, 7.7, 1.8 Hz), 7.54–7.47 (3H, m), 7.43 (1H, ddd, J=7.7, 4.9, 1.1 Hz), 7.39–7.28 (4H, m), 7.18 (1H, d, J=15.8Hz), 7.17 (1H, d, J=2.2 Hz), 6.87 (1H, dd, J=8.8, 2.2 Hz), 2.99 (6H, s).

Example 65

(E)-5-Formylamino-1-(2-pyridyl)-2-styryl-1H-benzimidazole

To a solution of (E)-5-amino-1-(2-pyridyl)-2-styryl-1H-benzimidazole (300 mg, 0.96 mmol) in formic acid (5 ml) was added acetic anhydride (1 ml) via syringe and the reaction mixture was warmed to 50° C. for 1 h. Volatiles were removed under reduced pressure and the residual viscous oil was poured into saturated aqueous sodium bicarbonate solution (50 ml) and the aqueous mixture was extracted with ethyl acetate (100 ml). The organic extract was washed consecutively with water (50 ml) and brine (50 ml), dried (sodium sulfate) and concentrated in vacuo. Recrystallization of the residue from ethyl acetate afforded 50 mg (15%) of the titled compound as light brown solids. MW: 340.39; mp: 189.9–192.1° C.; $^1$H-NMR (DMSO-d$_6$) δ: 10.26 (1H, br.s), 8.81–8.73 (1H, m), 8.30 (1H, d, J=1.8 Hz), 8.18 (1H, ddd, J=7.7, 7.7, 1.8 Hz), 8.10–8.05 (1H, m), 7.87 (1H, d, J=16.1 Hz), 7.73 (1H, d, J=7.7 Hz), 7.66–7.55 (3H, m), 7.44–7.30 (5H, m), 7.16 (1H, d, J=16.1 Hz).

Example 66

(E)-5-Acetylamino-1-(2-pyridyl)-2-styryl-1H-benzimidazole (E)-5-Amino-1-(2-pyridyl)-2-styryl-1H-benzimidazole (199 mg, 0.64 mmol) was dissolved in acetic anhydride (2 ml) and the solution was allowed to maintain at room temperature for 30 min. Then the reaction mixture was poured into saturated aqueous sodium bicarbonate solution (50 ml) and the aqueous mixture was extracted with ethyl acetate (100 ml). The organic extract was washed consecutively with water (50 ml) and brine (50 ml), dried (sodium sulfate) and concentrated in vacuo. The residual solids were purified by column chromatography (silica gel, 50 g; n-hexane/ethyl acetate (1/2)) and then recrystallized from ethyl acetate to afford 139 mg (61%) of the titled compound as yellow solids. MW: 354.41; mp: 105.4–106.9° C.; $^1$H-NMR (CDCl$_3$) δ: 8.81–8.74 (1H, m), 7.99 (1H, ddd, J=7.7, 7.7, 1.8 Hz), 7.97 (1H, d, J=15.8 Hz), 7.84 (1H, d, J=1.5 Hz), 7.63 (1H, br.s), 7.58–7.43 (5H, m), 7.41–7.30 (4H, m), 7.12 (1H, d, J=15.8 Hz), 2.21 (3H, s).

Example 67

(E)-5-Methysulfonylamino-1-(2-pyridyl)-2-styryl-1H-benzimidazole

To a stirred solution of (E)-5-amino-1-(2-pyridyl)-2-styryl-1H-benzimidazole (162 mg, 0.52 mmol) in dichloromethane (3 ml) and pyridine (1 ml) was added a solution of methanesulfonyl chloride (63 mg, 0.55 mmol) in dichloromethane (2 ml) dropwise. The reaction mixture was stirred for 2 h at room temperature and then partitioned between ethyl acetate (50 ml) and saturated aqueous sodium bicarbonate solution (50 ml). The organic phase was separated and the aqueous phase was extracted with ethyl acetate (50 ml). The combined extracts were washed with brine (50 ml), dried (sodium sulfate) and concentrated in vacuo to give brown oil. It was purified by column chromatography (silica gel, 20 g; n-hexane/ethyl acetate (5/1)). Recrystallization of the residue from ethyl acetate afforded 70 mg (34%) of the titled compound as off white solids. MW: 390.47; mp: 133.5–134.9° C.; $^1$H-NMR (CDCl$_3$) δ: 8.79 (1H, dd, J=5.1, 1.8 Hz), 8.02 (1H, d, J=16.1 Hz), 7.99 (1H, ddd, J=7.7,7.7, 1.8 Hz), 7.67 (1H, d, J=2.2 Hz), 7.55–7.46 (4H, m), 7.43 (1H, d, J=8.8 Hz), 7.41–7.30 (3H, m), 7.23 (1H, dd, J=8.8, 2.2 Hz), 7.10 (1H, d, J=16.1 Hz), 6.86 (1H, br.s), 3.00 (3H, s).

Example 68

(E)-Carbamoylamino-1-(2-pyridyl)-2-styryl-1H-benzimidazole

To a stirred solution of (E)-5-amino-1-(2-pyridyl)-2-styryl-1H-benzimidazole (199 mg, 0.64 mmol) in tetrahydrofuran (5 ml) was added trimethylsilyl isocyanate (300 mg, 2.6 mmol). The reaction mixture was stirred for 5 h at room temperature and concentrated in vacuo. The residue was purified by column chromatography (silica gel, 50 g; ethyl acetate ) and recrystallized from ethyl acetate/ethanol to give 13 mg (6%) of the titled compound as white solids. MW: 355.40; mp:>230° C.; $^1$H-NMR (CDCl$_3$) δ: 8.81–8.77 (1H, m), 8.01 (1H, d, J=16.1 Hz), 8.02 (1H, ddd, J=7.7, 7.7, 2.2 Hz), 7.70 (1H, d, J=2.2 Hz), 7.55–7.21 (9H, m), 7.11 (1H, d, J=16.1 Hz), 6.41 (1H, br.s), 4.67 (2H, br.s).

Example 69

(E)-1-(2-Pyridyl)-2-styryl-5-methoxy-1H-benzimidazole oxalate

Free base of the titled compound was prepared from 4-methoxy-2-nitroaniline according to the preparation of (E)-1-(2-pyridyl)-2-styryl-5-trifluoromethyl-1H-benzimidazole (Example 57). The free base and oxalic acid were dissolved into ethyl acetate. Concentration and recrystallization from ethyl acetate/n-hexane yielded the titled compound. MW: 417.42; mp: 187.0–188.0° C.; $^1$H-NMR (DMSO-d$_6$) δ: 8.76 (1H, dd, J=5.0, 1.3 Hz), 8.17 (1H, td, J=7.8,2.0 Hz), 7.85 (1H, d, J=15.8 Hz), 7.72 (1H, d, J=8.1 Hz), 7.65–7.58 (3H, m), 7.42–7.30 (4H, m), 7.26 (1H, d, J=2.2 Hz), 7.17 (1H, d, J=16.1 Hz), 6.90 (1H, dd, J=8.8, 2.6 Hz), 3.83 (3H, s).

Example 70

(E)-5-Ethoxyl-1-(2-pyridyl)-2-styryl-1H-benzimidazole oxalate

Free base of the titled compound was prepared from 4-ethoxy-2-nitroaniline according to the preparation of (E)-1-(2-pyridyl)-2-styryl-5-trifluoromethyl-1H-benzimidazole (Example 57). The free base and oxalic acid were dissolved into ethyl acetate. Concentration and recrystallization from ethyl acetate/n-hexane yielded the titled compound. MW: 435.05; mp: 215.5–216.0° C.; $^1$H-NMR (DMSO-d$_6$) δ: 8.78–8.75 (1H. m), 8.17 (1H, td, J=7.7, 1.8 Hz), 7.85 (1H, d, J=15.8 Hz), 7.72 (1H, d, J=8.1 Hz), 7.65–7.59 (3H, m), 7.44–7.33 (4H, m), 7.24 (1H, d, J=2.6 Hz), 7.18 (1H, d, J=15.8 Hz), 6.89 (1H, dd, J=8.8, 2.2 Hz), 4.10 (2H, q, J=7.0 Hz), 1.37 (3H, t, J=7.0 Hz).

Example 71

(E)-5-Isopropoxy-1-(2-pyridyl)-2-styryl-1H-benzimidazole oxalate

According to a literature procedure (Sala, T.; Sargent, M. V. *J. Chem. Soc. Perkin Trans. I.* 1979, 2593.), to a solution of (E)-5-hydroxy-1-(2-pyridyl)-2-styryl-1H-benzimidazole (63.8 mg, 0.2 mmol) in N,N-dimethylformamide (2 ml), potassium carbonate (140 mg, 1.0 mmol) and 2-bromopropane (0.2 ml, 2.0 mmol) was added at room temperature. This resulting mixture was stirred at room temperature for 19 h. To this mixture, ice-cold water (10 ml) was added and the whole was extracted with ethyl acetate and n-hexane (1:1, 2×20 ml). Combined organic layer was washed with water (2×20 ml), brine (20 ml), dried (magnesium sulfate) and filtered. The filtrate was concentrated and the residue was purified by column chromatography (silica gel, 10 g; n-hexane/ethyl acetate (5/1) to afford the desired compound (9.3 mg, 13%); $^1$H-NMR (CDCl$_3$) δ: 8.78–8.75 (1H, m), 8.01–7.79 (2H, m), 7.54–7.22 (8H, m), 7.14 (1H, d, J=16.11 Hz), 6.99–6.87 (2H, m), 4.65–4.55 (1H, m), 1.39 (6H, d, J=5.9 Hz). The free base and oxalic acid were dissolved into ethyl acetate. Concentration and recrystallization from ethyl acetate/n-hexane yielded the titled compound. MW: 445.48; mp: 165.0–166.0° C.

Example 72

(E)-5-Hydroxy-1-(2-pyridyl-2-styryl-1H-benzimidazole

Free base of the titled compound was prepared from (E)-5-methoxy-1-(2-pyridyl)-2-styryl-1H-benzimidazole according to the preparation of (E)-2-(3-Hydroxystyryl)-1-(2-pyridyl)-2-styryl-5-trifluoromethyl-1H-benzimidazole (Example 32). The free base and oxalic acid were dissolved into ethyl acetate. Concentration and recrystallization from ethyl acetate/n-hexane yielded the titled compound. MW: 358.68; mp: 261.0–261.5° C.; $^1$H-NMR (DMSO) δ: 9.35 (1H, br.s), 8.77–8.74 (1H, m), 8.16 (1H, td, J=7.7, 1.8 Hz), 7.83 (1H, d, J=16.1 Hz), 7.70 (1H, d, J=8.1 Hz), 7.63–7.58 (3H, m), 7.42–7.33 (3H, m), 7.26 (1H, d, J=8.8 Hz), 7.16 (1H, d, J=16.1 Hz), 7.04 (1H, d, J=1.8 Hz), 6.77 (1H, dd, J=8.6, 2.4 Hz).

Example 73

(E)-1-(2-Pyridyl)-2-styryl-5-trifluoromethoxy-1H-benzimidazole

The titled compound was prepared from 2-nitro4-trifluoromethoxyaniline according to the preparation of (E)-1-(2-pyridyl)-2-styryl-5-trifluoromethyl-1H-benzimidazole (Example 57). MW: 381.36; mp: 92.0–93.0° C.; $^1$H-NMR (CDCl$_3$) δ: 8.81–8.77 (1H, m), 8.02 (1H, d, J=16.5 Hz), 8.05–7.98 (1H, m), 7.71–7.68 (1H, m), 7.54–7.45 (4H, m), 7.45 (1H, d, J=8.8 Hz), 7.42–7.30 (3H, m), 7.17–7.10 (1H, m), 7.10 (1H, d, J=16.1 Hz)

Example 74

(E)-5.6-Dimethyl-1-(2-pyridyl)-2-styryl-1H-benzimidazole 1. (E)-5,6-Dimethyl-2-styryl-1H-benzimidazole A mixture of 2,5,6-trimethyl-1H-benzimidazole (1.5 g, 9.4 mmol) and benzaldehyde (5.0 g, 47 mmol) was heated to 200° C. for 3 h in a sealed tube. The reaction mixture was cooled to room temperature and then ether (50 ml) was added. The precipitated solids were collected by filtration to afford 300 mg (13%) of (E)-5,6-dimethyl-2-styryl-1H-benzimidazole as light yellow solids. $^1$H-NMR (CDCl$_3$) δ: 8.39–8.33 (1H, m), 7.58–7.47 (2H, m), 7.24–7.16 (5H, m), 6.82 (1H, d, J=16.5 Hz), 5.20 (1H, br.s), 2.13 (6H, s).

2. (E)-5,6-Dimethyl-1-(2-pyridyl)-2-styryl-1H-benzimidazole

The titled compound was prepared from 5,6dimethyl-2-styryl-1H-benzimidazole and 2-fluoropyridine according to the preparation of (E)-1-(2-pyridyl)-2-styryl-1H-benzimidazole (Example 1, method B). MW: 325.42; mp: 135.8–137.0° C.; $^1$H-NMR (CDCl$_3$) δ: 8.77 (1H, ddd, J=4.8, 1.8, 0.7 Hz), 7.98 (1H, ddd, J=7.7, 7.7, 1.8 Hz), 7.94 (1H, d, J=16.1 Hz), 7.59 (1H, s) 7.55–7.42 (4H, m), 7.38–7.26 (3H, m), 7.23 (1H, s), 7.12 (1H, d, J=16.1 Hz), 2.39 (3H, s), 2.35 (3H, s).

Example 75

(E)-6-Methyl-1-(2-pyridyl)-2-styryl-1H-benzimidazole 1. 5-Methyl-2-nitro-N-(2-pyridyl)aniline Nitric acid (100 ml) and 3-methyl-N-(2-pyridyl)aniline (Hirota, M.; Kobayashi, K. *Bull Chem. Soc. Jpn.* 1981, 54, 1583) (16.8 g, 91.2 mmol) was mixed with ice cooling, the ice bath was removed and the reaction mixture was stirred for 40 h at room temperature. The reaction mixture was poured into saturated aqueous sodium bicarbonate solution (200 ml), the aqueous mixture was basified with the addition of potassium carbonate and the resulting basic solution was extracted with ethyl acetate (500 ml). The organic extracts were washed with water (50 ml) and brine (50 ml), dried (magnesium sulfate) and concentrated to dryness. The residue was purified by column chromatography (silica gel, 350 g; n-hexane/ethyl acetate (9/1)) to give 3.85 g (18%) of the titled compound as yellow solids. $^1$H-NMR (CDCl$_3$) δ: 10.21 (1H, br.s), 8.54 (1H, s), 8.38–8.32 (1H, m), 8.13 (1H, d J=8.8 Hz), 7.68–7.60 (1H, m), 6.98–6.92 (2H, m), 6.80–6.70 (1H, m), 2,42 (3H, s).

2. 2-Amino-5-methyl-N-(2-pyridyl)aniline

A mixture of 5-methyl-2-nitro-N-(2-pyridyl)aniline (3.8 g, 16.6 mmol), 5% palladium on carbon (500 mg) in ethanol (100 ml) was stirred under a hydrogen atmosphere for 3 h. The mixture was filtered through a pad of celite and the filtrate was concentrated to dryness to give 3.3 g (quant.) of the titled compound as gray solids. $^1$H-NMR (CDCl$_3$) δ: 8.17–8.10 (1H, m), 7.46–7.38 (1H, m), 7.00 (1H, s), 6.90 (1H, d, J=8.1 Hz), 6.76–6.62 (2H, m), 6.46–6.39 (1H, m), 6.29 (1H, br.s), 3.71 (2H, br.s), 2.24 (3H, s).

3. (E)-6-Methyl-1-(2-pyridyl)-2-styryl-1H-benzimidazole

The titled compound was prepared from 2-amino-5-methyl-N-(2-pyridyl)aniline and (E)-cinnamoyl chloride according to the preparation of (E)-1-(2-pyridyl)-2-styryl-1H-benzimidazole (Example 1, method A). MW: 311.39; mp: 164.0–164.9° C.; $^1$H-NMR (CDCl$_3$) δ: 8.80–8.76 (1H, m), 8.03–7.92 (2H, m), 7.71 (1H, d, J=8.1 Hz), 7.54–7.42 (4H, m), 7.38–7.23 (4H, m), 7.19–7.14 (1H, m), 7.11 (1H, d, J=16.1 Hz), 2.46 (3H, s).

Example 76

(E)-6-Methoxy-1-(2-pyridyl)-2-styryl-1H-benzimidazole oxalate

Free base of the titled compound was prepared from 5-methoxy-2-nitroaniline according to the preparation of (E)-1-(2-pyridyl)-2-styryl-5-trifluoromethyl-1H-benzimidazole (Example 57). The free base and oxalic acid were dissolved into ethyl acetate. Concentration and recrystallization from ethyl acetate-hexane yielded the titled compound. MW: 417.42; mp: 172.0–174.0° C.; $^1$H-NMR (DMSO) δ: 8.78–8.76 (1H, m), 8.18 (1H, td, J=7.8, 2.1 Hz), 7.78 (1H, d, J=16.1 Hz), 7.74 (1H, d, J=8.1 Hz), 7.66–7.55 (4H, m), 7.41–7.32 (3H, m), 7.11 (1H, d, J=15.8 Hz), 6.98–6.91 (2H, m), 3.75 (3H, s).

Example 77

(E)-5-Methyl-2-(4-methoxystyryl-1-(2-pyridyl)-1H-benzimidazole hydrochloride Free base of the titled compound was prepared from 4-methyl-2-nitroaniline and (E)-4-methoxycinnamoyl chloride according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate/ethanol yielded the titled compound. MW: 377.88; mp: 220.8–221.9° C.; $^1$H-NMR (DMSO) δ: 8.84–8.79 (1H, m), 8.36–8.24 (2H, m), 7.88 (1H, d, J=8.1 Hz), 7.78 (1H, dd, J=7.7, 4.8 Hz), 7.68–7.60 (3H, m), 7.46 (1H, d, J=8.4 Hz), 7.36–7.30 (1H, m), 7.05–6.95 (3H, m), 3.83 (3H, s), 3.79 (3H, s).

Example 78

(E)-2-[2-(Cyclohexyl)ethenyl]-5-methyl-1-(2-pyridyl)-1H-benzimidazole oxalate Free base of the titled compound was prepared from 4-methyl-2-amino-N-(2-pyridyl)aniline and (E)-3-Cyclohexylacryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 407.47; mp: 141.0–142.0° C.; $^1$H-NMR (DMSO) δ: 8.73–8.71 (1H, m), 8.14 (1H, t, J=7.0 Hz), 7.61–7.56 (2H, m), 7.46 (1H, s), 7.26 (1H, d, J=8.1 Hz), 7.05 (1H, d, J=8.1 Hz), 6.92 (1H, dd, J=15.8, 7.0 Hz), 6.38 (1H, d, J=15.8 Hz), 2.42 (3H, s), 2.25–2.10 (1H, m), 1.80–1.55 (5H, m), 1.40–1.05 (5H, m).

Example 79

(E)-2-[2-(3-Furyl)ethenyl]-5-methyl-1-(2-pyridyl)-1H-benzimidazole oxalate

Free base of the titled compound was prepared from 4-methyl-2-amino-N-(2-pyridyl)aniline and (E)-3-(3-furyl) acryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate-hexane yielded the titled compound. MW: 391.38; mp: 197.0–198.0° C.; $^1$H-NMR (DMSO) δ: 8.78–8.74 (1H, m), 8.16 (1H, td, J=7.7, 2.2 Hz), 8.05 (1H, br.s), 7.77 (1H, d, J=15.8 Hz), 7.70–7.67 (2H, m), 7.65–7.59 (1H, m), 7.51 (1H, br.s), 7.32 (1H, d, J=8.4 Hz), 7.10–7.06 (1H, m), 6.89 (1H, d, J=15.8 Hz), 6.81 (1H, br.s), 2.44 (3H, s).

Example 80

(E)-5-Methyl-1-(2-pyridyl)-2-[2-(2-thienyl)ethenyl]-1H-benzimidazole oxalate Free base of the titled compound was prepared from 4-methyl-2-amino-N-(2-pyridyl)aniline and (E)-3-(2-thienyl)acryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 417.42; mp: 181.5–182.0° C.; $^1$H-NMR (DMSO) δ: 8.78–8.72 (1H, m), 8.16 (1H, t, J=7.7 Hz), 8.00 (1H, d, J=15.8 Hz), 7.69 (1H, d, J=8.1 Hz), 7.62–7.50 (3H, m), 7.39 (1H, br.s), 7.31 (1H, d, J=8.1 Hz), 7.15–7.05 (2H, m), 6.86 (1H, d, J=15.8 Hz), 2.42 (3H, s).

Example 81

(E)-5-Fluoro-(4-methoxystyryl)-1-(2-pyridyl)-1H-benzimidazole hydrochloride

Free base of the titled compound was prepared from 4-fluoro-2-amino-N-(2-pyridyl)aniline and (E)-4-methoxycinnamoyl chloride according to the preparation of (E)-1-(2-pyridyl)-2-styryl-1H-benzimidazole (Example 1, method A). The free base was treated with a 10% methanol solution of hydrogen chloride and concentrated to dryness. The residue was recrystallized from ethyl acetate/ethanol to give the titled compound. MW: 381.84; mp: 204.0–206.0° C.; $^1$H-NMR (CDCl$_3$) δ: 9.01 (1H, d, J=16.1 Hz), 8.86 (1H, dd, J=4.8, 2.0 Hz), 8.18 (1H, ddd, J=7.7, 7.7, 2.0 Hz), 7.83 (1H, dd, J=7.9, 2.3 Hz), 7.76 (1H, d, J=7.9 Hz), 7.69 (1H, dd, J=7.4, 4.8 Hz), 7.59 (2H, d J=8.7 Hz), 7.40 (1H, dd, J=9.0, 4.2 Hz), 7.17 (1H, ddd, J=9.0, 9.0, 2.3 Hz), 6.85 (2H, d, J=8.7 Hz), 6.78 (1H, d, J=16.1 Hz), 3.82 (3H, s).

Example 82

(E)-2-[2-(Cyclohexyl)ethenyl]-5-fluoro-1-(2-pyridyl)-1H-benzimidazole

The titled compound was prepared from 4-fluoro-2-amino-N-(2-pyridyl)aniline and (E)-3-Cyclohexylacryloyl chloride according to the preparation of (E)-1-(2-pyridyl)-2-styryl-1H-benzimidazole (Example 1, method A). MW: 321.40; mp: 109.1–110.1° C.; $^1$H-NMR (CDCl$_3$) δ: 8.76–8.72 (1H, m), 7.97 (1H, ddd, J=7.7, 7.7, 2.0 Hz), 7.47–7.40 (3H, m), 7.34 (1H, dd, J=9.0, 4.8 Hz), 7.11 (1H, dd, J=15.7, 7.1 Hz), 6.97 (1H, ddd, J=9.0,9.0,2.5 Hz), 6.38 (1H, dd, J=15.7, 1.3 Hz), 2.27–2.10 (1H, m), 1.84–1.57 (5H, m), 1.37–1.09 (5H, m).

Example 83

(E)-5-Fluoro-2-[2-(3-furyl)ethenyl]-1-(2-pyridyl)-1H-benzimidazole

The titled compound was prepared from 4-fluoro-2-amino-N-(2-pyridyl)aniline and (E)-3-(3-Cyclohexylacryloyl chloride according to the preparation of (E)-1-(2-pyridyl)-2-styryl-1H-benzimidazole (Example 1, method A). MW: 305.31; mp: 168.0–170.0° C.; $^1$H-NMR (CDCl$_3$) δ: 8.82–8.76 (1H, m), 8.15 (1H, d, J=16.0 Hz), 8.04 (1H, ddd, J=7.7, 7.7, 1.8 Hz), 7.71 (1H, s), 7.60–7.50 (3H, m), 7.43–7.33 (2H, m), 7.05 (1H, ddd, J=9.1, 9.1, 2.5 Hz), 6.74 (1H, d, J=16.0 Hz), 6.53 (1H, s).

Example 84

(E)-5-Fluoro-1-(2-pyridyl)-2-[2-(2-(thienyl)ethenyl]-1H-benzimidazole oxalate

Free base of the titled compound was prepared from 4-fluoro-2-amino-N-(2-pyridyl)aniline and (E)-3-(2-thienyl)acryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 411.41; mp: 176.5–178.0° C.; $^1$H-NMR (DMSO) δ: 8.79–8.76 (1H, m), 8.19 (1H, td, J=7.6,1.6 Hz), 8.06 (1H, d, J=15.7 Hz), 7.76 (1H, d, J=8.1 Hz), 7.67–7.62 (1H, m), 7.60 (1H, d, J=8.1 Hz), 7.52 (1H, dd, J=9.6, 2.4 Hz), 7.47–7.41 (2H, m), 7.16–7.08 (2H, m), 6.85 (1H, d, J=15.7 Hz).

Example 85

(E)-5-Methoxy 2-(4-methoxystyryl)-1-(2-pyridyl)-1H-benzimidazole oxalate

Free base of the titled compound was prepared from 4-methoxy-2-amino-N-(2-pyridyl)aniline and (E)-4-methoxycinnamoyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 417.42; mp: 198.0–198.5° C.; $^1$H-NMR (DMSO) δ: 8.76–8.74 (1H, m), 8.16 (1H, td, J=7.7, 1.8 Hz), 7.80 (1H, d, J=16.1 Hz), 7.70 (1H, d, J=8.1 Hz), 7.63–7.58 (1H, m), 7.55 (2H, d, J=8.8 Hz), 7.33 (1H, d, J=8.8 Hz), 7.23 (1H, d, J=2.2 Hz) 7.00 (1H, d, J=16.1 Hz), 6.95 (2H, d, J=8.8 Hz), 6.88 (1H, dd, J=8.8, 2.2 Hz), 3.82 (3H, s), 3.78 (3H, s).

Example 86

(E)-2-(3-Methyl-1-butenyl)-5-methoxy-1-(2-pyridyl)-1H-benzimidazole oxalate

Free base of the titled compound was prepared from 4-methoxy-2-amino-N-(2-pyridyl)aniline and (E)-4-methyl-2-pentenoyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 383.41; mp: 140.0–141.0° C.; $^1$H-NMR (DMSO) δ: 8.71 (1H, d, J=3.7 Hz), 8.16–8.10 (1H, m), 7.64–7.56 (2H, m), 7.28 (1H, d, J=9.2 Hz), 7.19 (1H, d, J=2.2 Hz), 6.99–6.83 (2H, m), 6.37 (1H, d, J=15.8 Hz), 3.80 (3H, s), 2.52–2.42 (1H, m), 1.02 (6H, d, J=6.6 Hz).

Example 87

(E)-2-[2-(Cyclohexyl)ethenyl]-5-methoxy-1-(2-pyridyl)-1H-benzimidazole hydrochloride Free base of the titled compound was prepared from 4-methoxy-2-amino-N-(2-pyridyl)aniline and (E)-3-Cyclohexylacryloyl chloride according to the preparation of (E)-1-(2-pyridyl)-2-styryl-1H-benzimidazole (Example 1, method A). The free base was dissolved with a 10% methanol solution of hydrogen chloride (5 ml). Concentration and recrystallization from ethyl acetate-hexane yielded the titled compound. MW: 369.90; mp: 168.0–169.0° C.; $^1$H-NMR (DMSO) δ: 8.80–8.76 (1H, m), 8.24 (1H, td, J=7.7, 1.8 Hz), 7.82–7.71 (2H, m), 7.46 (1H, d, J=9.2 Hz), 7.34–7.25 (2H, m), 7.09 (1H, dd, J=9.2, 2.6 Hz), 6.42 (1H, dd, J=15.8, 1.1 Hz), 3.56 (3H, s), 2.40–2.20 (1H, m), 1.80–1.55 (5H, m), 1.40–1.05 (5H, m).

Example 88

(E)-2-[2-(3-Furyl)ethenyl]-1-(2-pyridyl)-5-methoxy-1H-benzimidazole oxalate

Free base of the titled compound was prepared from 4-methoxy-2-amino-N-(2-pyridyl)aniline and (E)-3-(3-furyl)acryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate-hexane yielded the titled compound. MW: 407.39; mp: 196.0–198.0° C.; $^1$H-NMR (DMSO) δ: 8.75–8.73 (1H, m), 8.16 (1H, td, J=7.7, 1.8 Hz), 8.04 (1H, br.s), 7.76–7.58 (4H, m), 7.33 (1H, d, J=8.8 Hz), 7.23 (1H, d, J=2.2 Hz), 6.90–6.80 (3H, m), 3.82 (3H, s).

Example 89

(E)-5-Methoxy-2-[2-(2-methyl-3-furyl)ethenyl]-1-(2-pyridyl)-1H-benzimidazole 1. (E)-3-(2-Methyl-3-furyl)acrylic acid To a stirred solution of diisopropylamine (1.82 g, 18 mmol) under a nitrogen atmosphere at −78° C. was added a 1.6 M n-hexane solution of n-butyl lithium (11.4 ml. 18 mmol). After 15 min., a solution of(E)-3-(3-furyl)acrylic acid (1.24 g, 9 mmol) and hexamethylphosphoramide (6 ml) in tetrahydrofuran (45 ml) during 25 min. After 25 min., methyl iodide (3 ml, 6.84 g, 48 mmol) was added during 5 min. The resulting mixture was stirred at ambient temperature for 80 min. The reaction was quenched by adding 2N hydrogen chloride solution (10 ml), diluted with water (50 ml) and extracted with ethyl acetate (2×100 ml). The combined extracts were washed with brine (100 ml), dried (magnesium sulfate) and concentrated to dryness. The residue was dissolved into a mixture of toluene (8 ml) and methyl alcohol (2 ml) and 2 M n-hexane solution of trimethylsylildiazomethane (10 ml, 20 mmol) was added. After 20 min., the bulk of solvents was evaporated off and the residue was purified by column chromatography (silica gel, 150 g; n-hexane/ethyl acetate (10/0 to 9/1)) to give 1.20 g of a mixture of methyl (E)-3-(2-methyl-3-furyl)acrylate and unidentified compound. The mixture was dissolved into methanol (20 ml), a solution of potassium carbonate (1.38 g, 10 mmol) in water (2 ml) and stirred at room temperature overnight. Potassium carbonate (1.38 g, 10 mmol) added and the resulting suspension was heated to reflux for 4 h. After cooling, the reaction mixture was diluted with water (50 ml) and acidified with 10% aqueous solution of hydrogen chloride (50 ml). Solids were collected by suction, washed with water, and dried under vacuum at 50° C. for 70 min. to give 0.72 g (53%) of the titled compound as light brown solids. $^1$H-NMR (CDCl$_3$) δ: 7.66 (1H, d, J=15.8 Hz), 7.29 (1H, d, J=1.8 Hz), 6.52 (1H, d, J=1.8 Hz), 6.06 (1H, d, J=15.8 Hz), 2.41 (3H, s) (the proton of carboxylic acid was not observed)

2. (E)-5-Methoxy-2-[2-(2-methyl-3-furyl)ethenyl]-1-(2-pyridyl)-1H-benzimidazole (E)-3-(2-Methyl-3-furyl)acrylic acid (0.30 g, 2 mmol) was dissolved into thionyl chloride (5 ml) and the mixture was heated to reflux for 80 min. Volatiles were removed by evaporation to give crude (E)-3-(2-methyl-3-furyl)acryloyl chloride. The titled compound was prepared from 2-amino4-methoxy-N-(2-pyridyl)aniline (0.43 g, 2 mmol) and (E)-3-(2-methyl-3-furyl)acryloyl chloride obtained as above according to the preparation of (E)-1-(2-pyridyl)-2-styryl-1H-benzimidazole (Example 1, method A). Recrystallization from a mixture of isopropyl ether (3 ml) and ethyl acetate (3 ml) to give 0.10 g (16%) of the titled compound. MW: 331.38; mp: 139.0–140.0° C.; $^1$H-NMR (CDCl$_3$) δ: 8.75 (1H, dd, J=5.8, 2.2 Hz), 7.97 (1H, ddd, J=7.7, 7.7, 2.2 Hz), 7.79 (1H, d, J=15.8 Hz), 7.77–7.40 (2H, m), 7.33 (1H, d, J=8.8 Hz), 7.30 (1H, d, J=1.8 Hz), 7.24 (1H, d, J=2.0 Hz), 6.88 (1H, dd, J=9.2, 2.0 Hz), 6.72 (1H, d, J=15.8 Hz), 6.44 (1H, d, J=1.8 Hz), 3.89 (3H, s). 2.43 (3H, s).

Example 90

(E)-5-Methoxy-1-(2-Pyridyl)-2-[2-(2-thienyl)ethenyl]-1H-benzimidazole oxalate

Free base of the titled compound was prepared from 4-methoxy-2-amino-N-(2-pyridyl)aniline and (E)-3-(2-thienyl)acryloyl chloride according to the preparation of (E)-1-(2-pyridyl)-2-styryl-1H-benzimidazole Example 1, method A). The free base and oxalic acid were dissolved into ethyl acetate. Concentration and recrystallization from ethyl acetate/n-hexane yielded the titled compound. MW: 423.45; mp: 180.0–181.0° C.; $^1$H-NMR (DMSO) δ: 8.76 (1H, d, J=4.0 Hz), 8.18 (1H, td, J=7.3, 1.8 Hz), 7.99 (1H, d, J=15.8 Hz), 7.72 (1H, d, J=7.7 Hz), 7.65–7.56 (2H, m), 7.42 (1H, d, J=3.7 Hz), 7.34 (1H, d, J=8.8 Hz), 7.24 (1H, d, J=2.2 Hz), 7.14–7.09 (1H, m), 6.92–6.84 (2H, m), 3.83 (3H, s).

Example 91

(E)-5-Methoxy-1-(2-pyridyl)-2-[2-(3-thienyl)ethenyl]-1H-benzimidazole oxalate

Free base of the titled compound was prepared from 4-methoxy-2-amino-N-(2-pyridyl)aniline and (E)-3-(3-thienyl)acryloyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl acetate/n-hexane yielded the titled compound. MW: 423.45; mp: 203.0–204.0° C.; $^1$H-NMR (DMSO) δ: 8.77–8.74 (1H, m), 8.17–8.12 (1H, m), 7.89–7.82 (2H, m), 7.70 (1H, d, J=8.1 Hz), 7.64–7.56 (2H, m), 7.42 (1H, d, J=5.1 Hz), 7.35 (1H, d, J=9.0 Hz), 7.24 (1H, d, J=2.2 Hz), 7.00 (1H, d, J=16.1 Hz) 6.89 (1H, dd, J=9.0, 2.2 Hz) 3.83 (3H, s).

Example 92

(E)-1-(2-Pyridyl)-2-[2-(3-pyridyl)ethenyl]-1H-benzimidazole oxalate

Free base of the titled compound was prepared from 2-methyl-1-(2-pyridyl)-1H-benzimidazole and pyridine-3-Carboxaldehyde according to the preparation of (E)-1-(2-pyridyl)-2-[2-(2-pyridyl)ethenyl]-1H-benzimidazole dihydrochloride (Example 44). The free base and oxalic acid were dissolved into MeOH. Concentration and recrystallization from ethyl MeOH/EtOH yielded the titled compound. MW: 388.39; mp: 193.3–194.1° C. (decomposed); $^1$H-NMR (DMSO) δ: 8.86–8.81 (1H, m), 8.80–8.76 (1H, m), 8.53 (1H, dd, J=4.8, 1.5 Hz), 8.19 (1H, dt, J=7.8, 1.9 Hz), 8.12–8.05 (1H, m), 7.93 (1H, d, J=16.0 Hz), 7.76 (2H, d, J=7.9 Hz), 7.68–7.61 (1H, m), 7.51–7.25 (4H, m), 7.33 (1H, d, J=16.0 Hz).

Example 93

(E)-1-(2-Pyridyl)-2-[2-(4-pyridyl)ethenyl]-1H-benzimidazole oxalate

Free base of the titled compound was prepared from 2-methyl-1-(2-pyridyl)-1H-benzimidazole and pyridine4-carboxaldehyde according to the preparation of (E)-1-(2-pyridyl)-2-[2-(2-pyridyl)ethenyl]-1H-benzimidazole dihydrochloride Example 44). The free base and oxalic acid were dissolved into MeOH. Concentration and recrystalization from ethyl MeOH/Et$_2$O/n-hexane yielded the titled compound. MW: 388.39; mp: 203.6–205.3° C. (decomposed); $^1$H-NMR (DMSO) δ: 8.81–8.75 (1H, m), 8.62–8.55 (2H, m), 8.20 (1H, dt, J=1.9,7.7 Hz), 7.88 (1H, d, J=16.0 Hz), 7.81–7.74 (2H, m), 7.69–7.60 (3H, m), 7.52–7.46 (1H, m), 7.47 (1H, d, J=16.0 Hz) 7.40–7.28 (2H, m).

Example 94

(E)-1-(2-Pyridyl-2-[2-(2-imidazolyl)ethenyl]-1H-benzimidazole oxalate

Free base of the titled compound was prepared from 2-methyl-1-(2-pyridyl)-1H-benzimidazole and 2-imidazolcarboxaldehyde according to the preparation of (E)-1-(2-pyridyl)-2-[2-(2-pyridyl)ethenyl]-1H-benzimidazole dihydrochloride (Example 44).

The free base and oxalic acid were dissolved into MeOH. Concentration and recrystallization from ethyl EtOH/n-hexane yielded the titled compound. MW: 377.36; mp: 223.3–225.0° C. (decomposed); $^1$H-NMR (DMSO) δ: 8.70–8.65 (1H, m), 8.10 (1H, dd, J=7.7, 1.8 Hz), 7.68–7.51 (3H, m), 7.56 (1H, d, J=15.9 Hz), 7.36–7.12 (5H, m), 7.20 (1H, d, J=15.9 Hz).

Example 95

(E)-2-(4-Methylsulfonylstyryl)-1-(2-pyridyl-1H-benzimidazole

To a solution of (E)-2-(4-methylthiostyryl)-1-(2-pyridyl)-1H-benzimidazole (Example 44) (0.17 g, 0.50 mmol) and tetrabutylammonium bromide (10 mg) in $CH_2Cl_2$ (3.0 ml), a solution of oxone (0.39 g, 0.64 mmol) in $H_2O$ (4.0 ml) was added at rt. This mixture was stirred at room temperature for 2.5 h. After addition of $CH_2Cl_2$ (15 ml), organic later was washed with $H_2O$ (2×10 ml), brine (15 ml) dried ($MgSO_4$) and filtered. The filtrate was concentrated by evaporator and the residue was purified by column chromatography (silica gel, 20 g, n-hexane/ethyl acetate (1/2)). Recrystallization of the residue from ethyl acetate and hexane afforded the titled compound (0.13 g, 73%). MW: 375.45; mp: 152.0–154.0° C.; $^1$H-NMR (CDCl$_3$) δ: 8.82–8.78 (1H. m), 8.10–8.00 (2H, m), 7.92 (2H, d, J=8.4 Hz), 7.86 (1H, d, J=7.6 Hz), 7.68 (2H, d, J=8.64 Hz), 7.59–7.45 (3H, m), 7.42–7.28 (3H, m), 3.06 (3H, s).

Example 96

(E)-5-Methoxy-1-(2-pyridyl)-2-[2-(3-methyl-2-thienyl)ethenyl]-1H-benzimidazole oxalate Free base of the titled compound was prepared from 4-methoxy-2-amino-N-(2-pyridyl)aniline and (E)-3-(3-methyl-2-thienyl)acryloyl chloride (Sekiya, T.; Hiranuma, H.; Hata, S.; Mizogami, S.; Hanazuka, M.; Yamada, S. *J. Med. Chem.*, 1983, 26, 411) according to the preparation of (E)-1-(2-pyridyl)-2-styryl-1H-benzimidazole (Example 1, method A). The free base and oxalic acid were dissolved into ethyl acetate. Concentration and recrystallization from ethyl MeOH/n-hexane yielded the titled compound. MW: 437.48; mp: 192.5–193.5° C.; $^1$H-NMR (DMSO) δ: 8.65 (1H, dd, J=4.9, 1.8 Hz), 8.07 (1H, td, J=7.8, 1.9 Hz), 7.87 (1H, d, J=15.6 Hz), 7.62 (1H, d, J=8.1 Hz), 7.52 (1H, dd, J=7.4, 4.9 Hz), 7.37 (1H, d, J=5.1 Hz), 7.24 (1H, d, J=8.9 Hz), 7.16 (1H, d, J=2.3 Hz), 6.86 (1H, d, J=4.9 Hz), 6.79 (1H, dd, J=8.9,2.5 Hz), 6.67 (1H, d, J=15.6 Hz), 3.72 (3H, s), 2.22 (3H, s).

Example 97

(E)-5-Methoxy 2-(4-fluorostyryl)-1-(2-pyridyl)-1H-benzimidazole oxalate

Free base of the titled compound was prepared from 4-methoxy-2-amino-N-(2-pyridyl)aniline and (E)-4-fluorocinnamoyl chloride according to the preparation of (E)-1-(2-pyridyl)-2-styryl-1H-benzimidazole (Example 1, method A). The free base and oxalic acid were dissolved into ethyl acetate. Concentration and recrystallization from ethyl MeOH/n-hexane yielded the titled compound. MW: 435.41; mp: 205.5–206.0° C.; $^1$H-NMR (DMSO) δ: 8.66–8.63 (1H, m), 8.06 (1H, td, J=7.9, 1.9 Hz), 7.75 (1H, d, J=16.0 Hz), 7.62–7.48 (4H, m), 7.25 (1H, d, J=8.8 Hz), 7.15–7.11 (2H, m), 7.10 (1H, d, J=8.8 Hz), 7.02 (1H, d, J=16.0 Hz), 6.79 (1H, dd, J=8.8, 2.5 Hz), 3.72 (3H, s).

Example 98

(E)-5-Methoxy-1-(2-pyridyl)-2-[2-(2-thiazolyl)ethenyl]-1H-benzimidazole 1. 2-Methyl-2-(2-pyridyl)-1H-benzimidazole The titled compound was prepared from 4-methoxy-2-amino-N-(2-pyridyl)aniline and acetyl chloride according to the preparation of (E)-1-(2-pyridyl)-2-styryl-1H-benzimidazole (Example 1, method A).

2. (E)-5-Methoxy-1-(2-pyridyl)-2-[2-(2-thiazolyl)ethenyl]-1H-benzimidazole

Free base of the titled compound was prepared from 2-methyl-1-(2-pyridyl)-1H-benzimidazole and 2-thiazolecarboxaldehyde according to the preparation of (E)-1-(2-pyridyl)-2-[2-(2-pyridyl)ethenyl]-1H-benzimidazole dihydrochloride (Example 44). Recrystallization from ethyl acetate yielded the titled compound. MW. 334.40; mp: 156.5–158.0° C.; $^1$H-NMR (CDCl$_3$) δ: 8.79–8.71 (1H, m), 8.06 (1H, d, J=15.7 Hz), 8.03–7.94 (1H, m), 7.85 (1H, d, J=3.1 Hz), 7.58, 7.57 (1H, d×2, J=15.7 Hz), 7.54–7.42 (2H, m), 7.40–7.24 (3H, m), 6.99–6.91 (1H, m), 3.903, 3.900 (3H, sx2).

Example 99

(E)-5-Methoxy-2-[2-(5-methyl-2-thienyl)ethenyl]-1-(2-pyridyl)-1H-benzimidazole oxalate Free base of the titled compound was prepared from 4-methoxy-2-amino-N-(2-pyridyl)aniline and (E)-3-(5-methyl-2-thienyl)acryloyl chloride (Sekiya, T.; Hiranuma, H.; Hata, S.; Mizogami, S.; Hanazuka, M.; Yamada, S. *J. Med Chem.*, 1983, 26, 411) according to the preparation of (E)-1-(2-pyridyl)-2-styryl-1H-benzimidazole (Example 1, method A). The free base and oxalic acid were dissolved into ethyl acetate. Concentration and recrystallization from MeOH/n-hexane yielded the titled compound. MW: 437.48; mp: 190.0–191.0° C.; $^1$H-NMR (DMSO) δ: 8.67–8.63 (1H, m), 8.06 (1H, td, J=7.9, 1.9 Hz), 7.79 (1H, d, J=15.6 Hz), 7.59 (1H, d, J=7.9 Hz), 7.54–7.48 (1H, m), 7.22 (1H, d, J=8.7 Hz), 7.12–7.08 (2H, m), 6.77 (1H, dd, J=8.7, 2.5 Hz), 6.71–6.68 (1H, m), 6.66 (1H, d, J=15.6 Hz), 3.72 (3H, s), 2.33 (3H, s).

The chemical structures of the compounds prepared in the Examples 1 to 99 are summarized in the following tables.

TABLE (X²)ₙ — benzimidazole — CR³=CR²—R¹, N1 substituted with Ar—(X¹)ₘ

| Ex. # | Ar | X¹ | X² | R¹ | R² | R³ |
|---|---|---|---|---|---|---|
| 1 | 2-pyridyl | — | — | Ph. | H | H |
| 2 | 3-pyridyl | — | — | Ph. | H | H |
| 3 | 4-pyridyl | — | — | Ph. | H | H |
| 4 | 2-pyridyl | 3-CH₃ | — | Ph. | H | H |
| 5 | 2-pyridyl | 3-CF₃ | — | Ph. | H | H |
| 6 | 2-pyridyl | 3-CN | — | Ph. | H | H |
| 7 | 2-pyridyl | 3-carbamoyl | — | Ph. | H | H |
| 8 | 2-pyridyl | 4-CH₃ | — | Ph. | H | H |
| 9 | 2-pyridyl | 5-CH₃ | — | Ph. | H | H |
| 10 | 2-pyridyl | 5-CF₃ | — | Ph. | H | H |
| 11 | 2-pyridyl | 6-CH₃ | — | Ph. | H | H |
| 12 | 2-pyridyl | 6-F | — | Ph. | H | H |
| 13 | 2-pyridyl | 6-Cl | — | Ph. | H | H |
| 14 | 2-pyridyl | 6-CH₃O | — | Ph. | H | H |
| 15 | 2-pyrimidyl | — | — | Ph. | H | H |
| 16 | 2-pyrimidyl | 4-CF₃ | — | Ph. | H | H |
| 17 | 4-pyrimidyl | — | — | Ph. | H | H |
| 18 | 4-pyrimidyl | 6-Cl | — | Ph. | H | H |
| 19 | 2-pyrazinyl | — | — | Ph. | H | H |
| 20 | 2-thiazolyl | — | — | Ph. | H | H |
| 21 | 2-pyridyl | — | — | 2-CH₃—Ph. | H | H |
| 22 | 2-pyridyl | — | — | 2-F—Ph. | H | H |
| 23 | 2-pyridyl | — | — | 2-Cl—Ph. | H | H |
| 24 | 2-pyridyl | — | — | 2-CH₃O—Ph. | H | H |
| 25 | 2-pyridyl | — | — | 2,4-di F—Ph. | H | H |
| 26 | 2-pyridyl | — | — | 2,6-di F—Ph. | H | H |
| 27 | 2-pyridyl | — | — | 3-CH₃—Ph. | H | H |
| 28 | 2-pyridyl | — | — | 3-CF₃—Ph. | H | H |
| 29 | 2-pyridyl | — | — | 3-F—Ph. | H | H |
| 30 | 2-pyridyl | — | — | 3-Cl—Ph. | H | H |
| 31 | 2-pyridyl | — | — | 3-CH₃O—Ph. | H | H |
| 32 | 2-pyridyl | — | — | 3-HO—Ph. | H | H |
| 33 | 2-pyridyl | — | — | 3,4-di CH₃O—Ph. | H | H |
| 34 | 2-pyridyl | — | — | 4-CH₃—Ph. | H | H |
| 35 | 2-pyridyl | — | — | 4-C₂H₅—Ph. | H | H |
| 36 | 2-pyridyl | — | — | 4-isopropyl-Ph. | H | H |
| 37 | 2-pyridyl | — | — | 4-F—Ph. | H | H |
| 38 | 2-pyridyl | — | — | 4-CH₃O—Ph. | H | H |
| 39 | 2-pyridyl | — | — | 4-C₂H₅—Ph. | H | H |
| 40 | 2-pyridyl | — | — | 4-CH₃S—Ph. | H | H |
| 41 | 2-pyridyl | — | — | isopropyl | H | H |
| 42 | 2-pyridyl | — | — | 2-CH₃-2-propyl | H | H |
| 43 | 2-pyridyl | — | — | cyclohexyl | H | H |
| 44 | 2-pyridyl | — | — | 2-pyridyl | H | H |
| 45 | 2-pyridyl | — | — | 2-furyl | H | H |
| 46 | 2-pyridyl | — | — | 3-furyl | H | H |
| 47 | 4-pyridyl | — | — | 3-furyl | H | H |
| 48 | 2-pyridyl | — | — | 2-thienyl | H | H |
| 49 | 2-pyridyl | — | — | 3-thienyl | H | H |
| 50 | 2-pyridyl | — | — | 3-(2,5-di CH₃-thienyl) | H | H |
| 51 | 2-pyridyl | — | — | Ph. | Ph. | H |
| 52 | 2-pyridyl | — | — | Ph. | CH₃ | H |
| 53 | 2-pyridyl | — | — | Ph. | H | F |
| 54 | 2-pyridyl | — | — | cyclohexyl | H | CN |
| 55 | 2-pyridyl | — | — | CH₃ | CH₃ | H |
| 56 | 2-pyridyl | — | 4-CH₃ | Ph. | H | H |
| 57 | 2-pyridyl | — | 5-CF₃ | Ph. | H | H |
| 58 | 2-pyridyl | — | 5-CH₃ | Ph. | H | H |
| 59 | 2-pyridyl | — | 5-F | Ph. | H | H |
| 60 | 2-pyridyl | — | 5-CN | Ph. | H | H |
| 61 | 2-pyridyl | — | 5-NO₂ | Ph. | H | H |
| 62 | 2-pyridyl | — | 5-NH₂ | Ph. | H | H |
| 63 | 2-pyridyl | — | 5-CH₃—NH | Ph. | H | H |
| 64 | 2-pyridyl | — | 5-(diCH₃—N) | Ph. | H | H |
| 65 | 2-pyridyl | — | 5-formylation | Ph. | H | H |
| 66 | 2-pyridyl | — | 5-acetylamino | Ph. | H | H |

TABLE-continued

| Ex. # | Ar | $X^1$ | $X^2$ | $R^1$ | $R^2$ | $R^3$ |
|---|---|---|---|---|---|---|
| 67 | 2-pyridyl | — | 5-N-(methyl sulfonyl)amino | Ph. | H | H |
| 68 | 2-pyridyl | — | 5-carbamoyl amino | Ph. | H | H |
| 69 | 2-pyridyl | — | 5-$CH_3O$ | Ph. | H | H |
| 70 | 2-pyridyl | — | 5-$C_2H_5O$ | Ph. | H | H |
| 71 | 2-pyridyl | — | 5-isopropoxy | Ph. | H | H |
| 72 | 2-pyridyl | — | 5-OH | Ph. | H | H |
| 73 | 2-pyridyl | — | 5-$CF_3O$ | Ph. | H | H |
| 74 | 2-pyridyl | — | 5,6-di $CH_3$ | Ph. | H | H |
| 75 | 2-pyridyl | — | 6-$CH_3$ | Ph. | H | H |
| 76 | 2-pyridyl | — | 6-$CH_3O$ | Ph. | H | H |
| 77 | 2-pyridyl | — | 5-$CH_3$ | 4-$CH_3O$—Ph. | H | H |
| 78 | 2-pyridyl | — | 5-$CH_3$ | cyclohexyl | H | H |
| 79 | 2-pyridyl | — | 5-$CH_3$ | 3-furyl | H | H |
| 80 | 2-pyridyl | — | 5-$CH_3$ | 2-thienyl | H | H |
| 81 | 2-pyridyl | — | 5-F | 4-$CH_3O$—Ph. | H | H |
| 82 | 2-pyridyl | — | 5-F | cyclohexyl | H | H |
| 83 | 2-pyridyl | — | 5-F | 3-furyl | H | H |
| 84 | 2-pyridyl | — | 5-F | 2-thienyl | H | H |
| 85 | 2-pyridyl | — | 5-$CH_3O$ | 4-$CH_3O$—Ph. | H | H |
| 86 | 2-pyridyl | — | 5-$CH_3O$ | isopropyl | H | H |
| 87 | 2-pyridyl | — | 5-$CH_3O$ | cyclohexyl | H | H |
| 88 | 2-pyridyl | — | 5-$CH_3O$ | 3-furyl | H | H |
| 89 | 2-pyridyl | — | 5-$CH_3O$ | 2-$CH_3$-3-furyl | H | H |
| 90 | 2-pyridyl | — | 5-$CH_3O$ | 2-thienyl | H | H |
| 91 | 2-pyridyl | — | 5-$CH_3O$ | 3-thienyl | H | H |
| 92 | 2-pyridyl | — | — | 3-pyridyl | H | H |
| 93 | 2-pyridyl | — | — | 4-pyridyl | H | H |
| 94 | 2-pyridyl | — | — | 2-imidazolyl | H | H |
| 95 | 2-pyridyl | — | — | 4-methylsulfonyl-Ph. | H | H |
| 96 | 2-pyridyl | — | 5-$CH_3O$ | 3-$CH_3$-2-thienyl | H | H |
| 97 | 2-pyridyl | — | 5-$CH_3O$ | 4-F—Ph. | H | H |
| 98 | 2-pyridyl | — | 5-$CH_3O$ | 2-thiazolyl | H | H |
| 99 | 2-pyridyl | — | 5-$CH_3O$ | 5-$CH_3$-2-thienyl | H | H |

Ph.: phenyl;
$CH_3$: methyl;
C2H5: ethyl;
$CF_3$: trifluoromethyl;
$CH_3O$: methoxy;
$CH_3S$: methylthio;
F: fluoro;
Cl: chloro;
CN: cyano;
OH: hydroxy;
$NO_2$: nitro;
$NH_2$, NH, N: amino;

What is claimed is:

1. A compound of formula I:

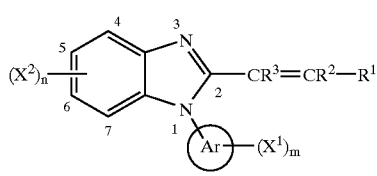

(I)

or a pharmaceutically acceptable salt thereof, wherein

Ar is a 6-membered monocyclic aromatic ring having two N atoms; and said heteroaryl being connected to the nitrogen atom on the benzimidazole through a carbon atom on the heteroaryl ring;

$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N-($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$X^2$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—$C_1$–$C_4$ alkyl)amino]$C_1$–$C_4$ alkyl, [N,N-di(($C_1$–$C_4$ alkyl)amino]$C_1$–$C_4$ alkyl, N—($C_1$–$C_4$ alkanoyl)amino, N—($C_1$–$C_4$ alkyl)-N—($C_1$–$C_4$ alkanoyl)amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, N-carbamoylamino, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl;

$R^1$ is selected from
hydrogen;
straight or branched $C_1$–$C_4$ alkyl optionally substituted with one to three substituent(s) wherein said substituents are independently selected from halo, hydroxy, $C_1$–$C_4$ alkoxy, amino, N—($C_1$–$C_4$ alkyl)amino and N,N-di($C_1$–$C_4$ alkyl)amino;
$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;
$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;
phenyl optionally substituted with one to three substituent(s) wherein said substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, [N—($C_1$–$C_4$ alkyl)amino]$C_1$–$C_4$ alkyl, [N,N-di($C_1$–$C_4$ alkyl)amino]$C_1$–$C_4$ alkyl, N—($C_1$–$C_4$ alkanoyl)amino, N—[($C_1$–$C_4$ alkyl)($C_1$–$C_4$ alkanoyl)]amino, N—[($C_1$–$C_4$ alkyl)sulfonyl]amino, N-[(halo-substituted $C_1$–$C_4$ alkyl)sulfonyl]amino, $C_1$–$C_4$ alkanoyl, carboxy, ($C_1$–$C_4$ alkoxy)carbonyl, carbamoyl, [N—($C_1$–$C_4$ alkyl)amino]carbonyl, [N,N-di($C_1$–$C_4$ alkyl)amino]carbonyl, cyano, nitro, mercapto, ($C_1$–$C_4$ alkyl)thio, ($C_1$–$C_4$ alkyl)sulfinyl, ($C_1$–$C_4$ alkyl)sulfonyl, aminosulfonyl, [N—($C_1$–$C_4$ alkyl)amino]sulfonyl and [N,N-di($C_1$–$C_4$ alkyl)amino]sulfonyl; and $R^2$ and $R^3$ are independently selected from:
hydrogen;
halo;
$C_1$–$C_4$ alkyl;
phenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_3$–$C_7$ cycloalkyl ring;
m is 0, 1, 2, 3, 4 or 5; and
n is 0, 1, 2, 3 or 4.

2. A compound according to claim 1, wherein
Ar is a 6-membered monocyclic aromatic ring having two N atoms; and
$X^1$ is independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N—($C_1$–$C_4$ alkanoyl)amino, $C_1$–$C_4$ alkanoyl, carboxy, carbamoyl, [N—($C_1$–$C_4$ alkyl)amino]carbonyl, [N,N-di($C_1$–$C_4$ alkyl)amino]carbonyl, cyano, nitro, mercapto and ($C_1$–$C_4$ alkyl)thio;

$X^2$ is independently selected from halo, $C_1$–$C_4$ alkyl, hydroxy, $C_1$–$C_4$ alkoxy, halo-substituted $C_{-C4}$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N—($C_1$–$C_4$ alkanoyl)amino, [($C_1$–$C_4$ alkyl)sulfonyl]amino, $C_1$–$C_4$ alkanoyl, carboxy, carbamoyl, N-carbamoylamino, cyano, nitro, mercapto and ($C_1$–$C_4$ alkyl)thio;

$R^1$ is selected from
hydrogen;
straight or branched $C_1$–$C_4$ alkyl optionally substituted with one to three substituent(s) wherein said substituents are independently selected from halo, hydroxy, $C_1$–$C_4$ alkoxy and amino;
$C_3$–$C_8$ cycloalkyl optionally substituted with one to three substituent(s) wherein said substituents are independently selected from halo, $C_1$–$C_4$ alkyl, hydroxy, $C_1$–$C_4$ alkoxy and amino;
$C_4$–$C_8$ cycloalkenyl optionally substituted with one to three substituent(s) wherein said substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;
phenyl optionally substituted with one to three substituent(s) wherein the substituents are independently selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, ($C_1$–$C_4$ alkoxy) $C_1$–$C_4$ alkyl, halo-substituted $C_1$–$C_4$ alkoxy, amino, ($C_1$–$C_4$ alkanoyl)amino, $C_1$–$C_4$ alkanoyl, carboxy, carbamoyl, ($C_1$–$C_4$ alkyl)thio, ($C_1$–$C_4$ alkyl)sulfinyl, ($C_1$–$C_4$ alkyl)sulfonyl, and aminosulfonyl; or $R^2$ and $R^3$ are independently selected from:
hydrogen;
halo;
$C_1$–$C_4$ alkyl;
phenyl optionally substituted with one to three substituent(s) wherein the substituents are independently selected from halo, $C_1$–$C_4$ alkyl, hydroxy, $C_1$–$C_4$ alkoxy, amino, N—($C_1$–$C_4$ alkyl)amino and N,N-di($C_1$–$C_4$ alkyl)amino;

or $R^1$ and $R^2$ can form, together with the carbon atom to which they are attached, a $C_5$–$C_7$ cycloalkyl ring;
m is 0, 1, 2, 3 or 4; and
n is 0, 1, 2 or 3.

3. A compound according to claim 2, wherein

Ar is a 6-membered monocyclic aromatic ring having two N atoms and $X^1$ is selected from halo, $C_1$–$C_4$ alkyl, halo-substituted $C_1$–$C_4$ alkyl, $C_1$–$C_4$ alkoxy, halo-substituted $C_1$–$C_4$ alkoxy, carbamoyl, [N—($C_1$–$C_4$ alkyl)amino]carbonyl, [N,N di($C_1$–$C_4$ alkyl)amino]carbonyl and cyano;

$X^2$ is selected from halo, $C_1$–$C_4$ alkyl, hydroxy, $C_1$–$C_4$ alkoxy, halo-substituted $C_1$–$C_4$ alkyl, hydroxy-substituted $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N-formylamino, N—($C_1$–$C_4$ alkanoyl)amino, [($C_1$–$C_4$ alkyl)sulfonyl]amino, N-carbamoylamino, cyano and nitro; and $R^1$ is selected from $C_1$–$C_4$ alkyl optionally substituted with one to three substituents wherein said substituents are independently selected from halo, hydroxy and amino;

$C_5$–$C_7$ cycloalkyl optionally substituted with one to three substituents wherein said substituents are independently selected from halo, hydroxy and amino;

phenyl optionally substituted with one or two substituent(s), said substituents being independently selected from halo, hydroxy, $C_1$–$C_4$ alkyl, $C_1$–$C_4$ alkoxy, halo-substituted $C_1$–$C_4$ alkyl, halo-substituted $C_1$–$C_4$ alkoxy, ($C_1$–$C_4$ alkyl)thio, $C_1$–$C_4$ alkylsulfonyl and amino; or $R^2$ and $R^3$ are independently selected from hydrogen;

halo;

$C_1$–$C_4$ alkyl; and phenyl optionally substituted from halo, hydroxy, amino, $C_1$–$C_4$ alkyl and $C_1$–$C_4$ alkoxy;

or $R^1$ and $R^2$ can form, together with the carbon atom to which they are attached, a $C_{5-6}$ cycloalkyl ring;

m is 0, 1, 2 or 3; and n is 0, 1 or 2.

4. A compound according to claim 3, wherein

Ar is pyrimidinyl;

$X^1$ is selected from halo, $C_1$–$C_4$ alkyl, halo-substituted $C_1$–$C_4$ alkyl, $C_1$–$C_4$ alkoxy, carbamoyl and cyano;

$X^2$ is selected from halo, $C_1$–$C_4$ alkyl, hydroxy, $C_1$–$C_4$ alkoxy, halo-substituted $C_1$–$C_4$ alkyl, halo-substituted $C_1$–$C_4$ alkoxy, amino, N—($C_1$–$C_4$ alkyl)amino, N,N-di($C_1$–$C_4$ alkyl)amino, N-formylamino, N—($C_1$–$C_4$ alkanoyl)amino, [($C_1$–$C_4$ alkyl)sulfonyl]amino, N-carbamoylamino, cyano and nitro;

$R^1$ is selected from (straight or branched) $C_1$–$C_4$ alkyl;

$C_5$–$C_7$ cycloalkyl;

phenyl optionally substituted with one or two substituent(s), said substituents being independently selected from halo, hydroxy, $C_1$–$C_4$ alkyl, $C_1$–$C_4$ alkoxy, halo-substituted $C_1$–$C_4$ alkyl, ($C_1$–$C_4$ alkyl)thio and $C_1$–$C_4$ alkylsulfonyl; or $R^2$ is selected from hydrogen, $C_1$–$C_4$ alkyl and phenyl;

$R^3$ is selected from hydrogen, halo, $C_1$–$C_4$ alkyl and cyano;

or $R^1$ and $R^2$ can form, together with the carbon atom to which they are attached, cyclohexyl; and m is 0, 1 or 2.

5. A compound according to claim 4, wherein

Ar is pyrimidinyl;

$X^1$ is selected from fluoro, chloro, methyl, methoxy, trifluoromethyl, carbamoyl and cyano;

$X^2$ is selected from fluoro, methyl, hydroxy, methoxy, ethoxy, isopropoxy, trifluoromethyl, trifluoromethoxy, amino, N-methylamino, N,N-dimethylamino, N-methylsulfonylamino, N-formylamino, N-acetylamino, N-carbamoylamino, cyano and nitro;

$R^1$ is selected from methyl, isopropyl, cyclohexyl, phenyl, which are optionally substituted with one to three substituents selected from methyl, ethyl, isopropyl, methoxy, ethoxy, fluoro, chloro and hydroxy;

$R^2$ is selected from hydrogen, methyl and phenyl;

or $R^1$ and $R^2$ can form, together with the carbon atom to which they are attached, cyclohexyl;

$R^3$ is selected from hydrogen, fluoro and cyano; and m is 0 or 1.

6. A compound according to claim 1, which is (E)-1-(2-Pyrimidyl)-2-styryl-1H-benzimidazole oxalate.

7. A pharmaceutical composition useful as anti-inflammatory and analgesic agents, which comprises a compound according to claim 1, and a pharmaceutically acceptable carrier.

8. A pharmaceutical composition for treating a disorder or condition in a mammal, selected from rheumatoid and osteoarthritis, pyrexia, asthma, bone resorption, cardiovascular diseases, nephrotoxicity, atherosclerosis, hypotension, shock, pain, cancer, Alzheimer disease, and other disorders and conditions, in which a pathological role of prostaglandins is implicated, comprising an amount of the compound of claim 1, or a pharmaceutically acceptable salt thereof, that is effective in treating such disorder or condition, and a pharmaceutically acceptable carrier.

9. A method of treating a disorder or a medical condition in which prostaglandins are implicated as pathogens, in a mammalian subject, which comprises administering to a mammal an effective cyclooxygenase-2 inhibitory amount of compound of claim 1 or a pharmaceutically acceptable salt thereof, that is effective in treating said disorder or medical condition.

10. A method of treating a disorder or condition in a mammal, selected from rheumatoid and osteoarthritis, pyrexia, asthma, bone resorption, cardiovascular diseases, nephrotoxicity, atherosclerosis, hypotension, shock, pain, cancer, Alzheimer disease and other disorders and conditions, in which a pathological role of prostaglandins are implicated, comprising administering to a mammal in need of such treatment an effective cyclooxygenase-2 inhibitory amount of the compound of claim 1, or a pharmaceutically acceptable salt thereof, that is effective in treating such disorder or condition, and a pharmaceutically acceptable carrier.

\* \* \* \* \*